United States Patent
Kunz et al.

(10) Patent No.: US 7,105,545 B2
(45) Date of Patent: Sep. 12, 2006

(54) N-P-PROPARGYLOXYPHENETHYL-THIOACETIC ACID AMIDES

(75) Inventors: Walter Kunz, Oberwil (CH); Clemens Lamberth, Basel (CH); Fredrik Cederbaum, Basel (CH); Martin Zeller, Muenchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/472,577

(22) PCT Filed: Apr. 2, 2002

(86) PCT No.: PCT/EP02/03623

§ 371 (c)(1),
(2), (4) Date: Sep. 23, 2003

(87) PCT Pub. No.: WO02/081437

PCT Pub. Date: Oct. 17, 2002

(65) Prior Publication Data

US 2004/0127739 A1    Jul. 1, 2004

(30) Foreign Application Priority Data

Apr. 3, 2001    (GB) ................ 0108339.3

(51) Int. Cl.
- *A01N 43/40* (2006.01)
- *A01N 43/06* (2006.01)
- *A01N 43/08* (2006.01)
- *A01N 37/44* (2006.01)
- *A01N 37/18* (2006.01)

(52) U.S. Cl. .............. 514/331; 514/438; 514/471; 514/538; 514/599; 546/233; 549/65; 549/493; 560/16; 564/74

(58) Field of Classification Search ........... 514/599, 514/538, 438, 471, 331; 560/16; 549/493; 549/65; 546/233; 564/74
See application file for complete search history.

(56) References Cited

U.S. PATENT DOCUMENTS 5,977,410 A * 11/1999 Fujii et al. ............. 564/347

6,683,211 B1 * 1/2004 Lamberth et al. ........... 564/175

FOREIGN PATENT DOCUMENTS

| WO | 00/41998 | * | 7/2000 |
| WO | 0187822 | | 11/2001 |

* cited by examiner

Primary Examiner—Peter G. O'Sullivan
(74) Attorney, Agent, or Firm—Rebecca Gegick

(57) ABSTRACT

The invention relates to N-propargyloxy-phenethyl thioacetic acid amide derivatives of the general formula (I) including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$ and $R_8$ are each independently hydrogen or alkyl, $R_9$ is hydrogen, optionally substituted alkyl, optionally substituted alkenyl or optionally substituted alkynyl, $R_{10}$ is optionally substituted aryl or optionally substituted heteroaryl, and Z is hydroxy, optionally substituted aryloxy, optionally substituted alkoxy, optionally substituted alkynyloxy, optionally substituted arylthio, optionally substituted alkylthio, optionally substituted alkynylthio, optionally substituted alkylsulfinyl, optionally substituted alkenysulfinyl, optionally substituted alkynylsulfinyl, optionally substituted alkylsulfonyl, optionally substituted alkenylsulfonyl, optionally substituted alkynylsulfonyl or a group $-O-CO-R_{11}$, $-O-CO-O-R_{11}$ or $-O-CO-CO-O-R_{11}$ wherein $R_{11}$ is hydrogen, optionally substituted alkyl, optionally substituted cycloalkyl, optionally substituted aryl or optionally substituted heteroaryl. These compounds possess useful plant protecting properties and may advantageously be employed in agricultural practice for controlling or preventing the infestation of plants by phytopathogenic microorganisms, especially fungi (I)

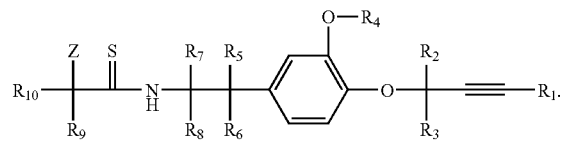

10 Claims, No Drawings

N-P-PROPARGYLOXYPHENETHYL-THIOACETIC ACID AMIDES

The present invention relates to novel N-phenethyl thioacetic acid amide derivatives of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to N-phenethyl thioacetic acid amide derivatives of the general formula I

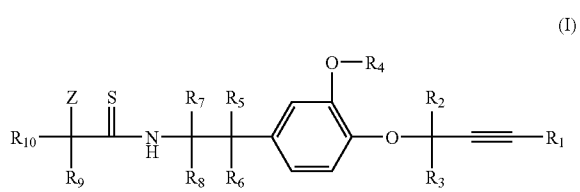

(I)

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl, $R_9$ is hydrogen, optionally substituted alkyl, optionally substituted alkenyl or optionally substituted alkynyl, $R_{10}$ is optionally substituted aryl or optionally substituted heteroaryl, and Z is hydroxy, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl, optionally substituted alkynylsulfonyl or a group —O—CO—$R_{11}$, —O—CO—O—$R_{11}$ or —O—CO—CO—O—$R_{11}$ wherein $R_{11}$ is hydrogen, optionally substituted alkyl, optionally substituted cycloalkyl, optionally substituted aryl or optionally substituted heteroaryl.

In the above definition aryl includes aromatic hydrocarbon rings like phenyl, naphthyl, anthracenyl, phenanthrenyl and biphenyl like 1,3-biphenyl and 1,4-biphenyl, with phenyl being preferred. The same definition applies where aryl is part of aryloxy or arylthio. Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may be optionally substituted. This means that they may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenylalkyl, it being possible in turn for all of the preceding groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl. Typical examples include 4-chlorophenyl, 4-bromophenyl, 3,4-dichlorophenyl, 4-chloro-3-fluorophenyl, 3-chloro-4-fluorophenyl, 4-methylphenyl, 4-ethylphenyl, 4-propargyloxyphenyl, 1-naphthyl, 2-naphthyl, 4-biphenylyl, 4'-chloro-4-biphenylyl, 5-chloro-thien2-yl, 5-methyl-thien-2-yl 5-methyl-fur-2-yl, 5,6,7,8-tetrahydro-1-naphthyl, 5,6,7,8-tetrahydro-2-naphthyl, 3,4-dioxomethylenyl -phenyl, 3,4-dioxoethylenyl-phenyl, 6-benzothienyl, 7-benzothienyl, 3-methylphenyl, 4-fluorophenyl, 4-ethenylphenyl, 4-ethynylphenyl, 4-propylphenyl, 4-isopropylphenyl, 4-tert.-butylphenyl, 4-ethoxyphenyl, 4-ethynyloxyphenyl, 4-phenoxyphenyl, 4-methylthiophenyl, 4-methylsulfonylphenyl, 4-cyanophenyl, 4-nitrophenyl, 4-methoxycarbonyl-phenyl, 3-bromophenyl, 3-chlorophenyl, 2-chlorophenyl, 2,4-dichlorophenyl, 3,4,5-trichlorophenyl, 3,4-difluorophenyl, 3,4-dibromophenyl, 3,4-dimethoxyphenyl, 3,4-dimethylphenyl, 3-chloro-4-cyanophenyl, 4-chloro-3-cyanophenyl, 3-bromo-4-methylphenyl, 4-methoxy-3-methylphenyl, 3-fluoro-4-methoxyphenyl, 4-chloro-3-methylphenyl, 4-chloro-3-trifluoromethyl-phenyl, 4-bromo-3-chlorophenyl, 4-trifluoromethylphenyl, 4-trifluoromethoxyphenyl, 4-methoxyphenyl, 4'-methyl -4-biphenylyl, 4'-trifluoromethyl-4-biphenylyl, 4'-bromo-4-biphenylyl, 4'-cyano-4-biphenyly 3'4'-dichloro-4-biphenylyl, etc.

Again, the same optional substituent may be present where aryl is part of aryloxy or arylthio.

Optionally substituted alkyl, alkenyl or alkynyl groups may carry one or more subsfituents selected from halogen, alkyl, alkoxy, alkylthio, cycloalkyl, phenyl, nitro, cyano, hydroxy, mercapto, alkylcarbonyl or alkoxycarbonyl. This also applies where alkyl, alkenyl or alkynyl is part of another substituent like alkoxy, alkylthio, alkylsulfinyl, alkylsulfonyl, alkenyloxy, alkenylthio, alkenylsulfinyl, alkenylsufonyl, alkynyloxy, alkynylthio, alkynylsulfinyl and alkynylsulfonyl.

Preferably, the number of substituents is no more than three with the exception of halogen, where the alkyl groups may be perhalogenated.

In the above definitions "halogen" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl.

A haloalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, etc.

The presence of at least one asymmetric carbon atom in the compounds of formula I means that the compounds may occur in optically isomeric and enantiomeric forms. Additionally, as a result of the presence of a possible aliphatic C=C double bond, geometric isomerism may also occur. Formula I is intended to include all those possible isomeric forms and mixtures thereof.

Preferred subgroups of compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy; alkenyloxy; alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; or $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; or $R_1$ is hydrogen, $C_1$–$C_8$alkyl or phenyl optionally substituted by one to three substituents selected from the group comprising $C_1$–$C_8$alkyl, $C_1$–$C_8$haloalkyl, $C_1$–$C_8$alkoxy, $C_{1-C_8}$haloalkoxy, $C_1$–$C_8$alkylthio, $C_1$–$C_8$haloalkylthio, halogen, cyano, nitro and $C_1$–$C_8$alkoxycarbonyl; or $R_1$ is hydrogen, $C_1$–$C_8$alkyl or $C_3$–$C_8$cycloalkyl; or $R_1$ is hydrogen or $C_1$–$C_4$alkyl; or $R_2$ and $R_3$ are independently of each other hydrogen or $C_1$–$C_4$alkyl; or $R_2$ and $R_3$ are hydrogen; or $R_4$ is $C_1$–$C_8$alkyl, $C_2$–$C_8$alkenyl, or $C_2$–$C_8$alkynyl; or $R_4$ is $C_1$–$C_6$alkyl; or $R_4$ is $C_1$–$C_4$alkyl, or $R_4$ is methyl or ethyl, especially methyl; or $R_5$, $R_6$, $R_7$ and $R_8$ are independently of each other hydrogen or $C_1$–$C_4$alkyl; or $R_5$, $R_6$ and $R_7$ are hydrogen and $R_8$ is hydrogen, methyl or ethyl, preferably hydrogen or methyl; or $R_5$, $R_6$, $R_7$ and $R_8$ are hydrogen; or $R_9$ is hydrogen, $C_1$–$C_4$alkyl, $C_1$–$C_4$haloalkyl, $C_3$–$C_4$alkenyl or $C_3$–$C_4$alkynyl; or $R_9$ is hydrogen or $C_1$–$C_4$alkyl; or $R_9$ is hydrogen; or $R_{10}$ is aryl or heteroaryl, each optionally substituted with substituents selected from the group comprising alkyl, alkenyl, alkynyl, cycloalkyl, cycloalkyl-alkyl, phenyl and phenylalkyl, where all these groups may be substituted with one or more halogen atoms; alkoxy; alkenyloxy; alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl and alkynyloxycarbonyl; or $R_{10}$ is phenyl, naphthyl or biphenyl, each optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; or $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; or $R_{11}$ is hydrogen, $C_1$–$C_6$alkyl or $C_3$–$C_6$-cycloalkyl;, or $R_{11}$ is hydrogen or $C_1$–$C_4$-alkyl; or p1 $R_{11}$ is hydrogen or methyl; or $R_{11}$ is methyl, or Z is hydroxy, optionally substituted aryloxy or arylthio wherein In each the aryl may be optionally substituted by one or more substituents selected from the group comprising halogen, $C_1$–$C_8$alkoxy, $C_2$–$C_8$alkenyloxy, $C_2$–$C_8$alkynyloxy, $C_1$–$C_8$alkoxy-$C_1$–$C_8$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–1$C_8$alkylamino, di-$C_1$–$C_8$alkylamino, carboxyl and $C_1$–$C_8$alkoxycarbonyl; or is optionally substituted $C_1$–$C_8$alkoxy, optionally substituted $C_2$–$C_8$alkenyloxy, optionally substituted $C_2$–$C_8$alkynyloxy, optionally substituted $C_1$–$C_8$alkylthio, optionally substituted $C_2$–$C_8$alkenylthio, optionally substituted $C_2$–$C_8$alkynylthio, optionally substituted $C_1$–$C_8$alkylsulfinyl, optionally substituted $C_2$–$C_8$alkenylsulfinyl, optionally substituted $C_2$–$C_8$alkynylsulfinyl, optionally substituted $C_1$–$C_8$alkylsulfonyl, optionally substituted $C_2$–$C_8$alkenylsulfonyl; optionally substituted $C_2$–$C_8$alkynylsulfonyl wherein each alkyl, alkenyl or alkynyl group may carry one or more substituents selected from the group comprising halogen, $C_1$–$C_4$alkyl, $C_1$–$C_4$alkoxy, $C_1$–$C_4$alkylthio, $C_3$–$C_6$cycloalkyl, nitro, cyano, hydroxy, phenyl, mercapto, $C_1$–$C_4$alkylcarbonyl and $C_1$–$C_4$alkoxycarbonyl; or is a group —O—CO—$R_{11}$, —O—CO—O—$R_{11}$ or —O—CO—CO—O—$R_{11}$ wherein $R_{11}$ is hydrogen, $C_1$–$C_4$-alkyl or $C_3$–$C_6$-cycloalkyl; or Z is hydroxy; $C_1$–$C_8$alkoxy, $C_2$–$C_8$alkenyloxy, $C_2$–$C_8$alkynyloxy, $C_1$–$C_8$alkoxy-$C_1$–$C_8$alkoxy, $C_2$–$C_8$alkenyloxy-$C_1$–$C_8$alkoxy, $C_2$–$C_8$alkynyloxy-$C_1$–$C_8$alkoxy, $C_1$–$C_8$haloalkoxy, $C_3$–$C_8$cycloalkyl-$C_1$–$C_8$alkoxy, $C_1$–$C_8$alkylthio, $C_2$–$C_8$alkenylthio, $C_2$–$C_8$alkynylthio, $C_1$–$C_8$haloalkylthio, $C_3$–$C_8$cycloalkyl-$C_1$–$C_8$alkylthio, $C_1$–$C_8$alkylsulfinyl, $C_1$–$C_8$alkylsulfonyl, $C_2$–$C_8$alkenylsulfinyl, $C_2$–$C_8$alkenylsulfonyl, $C_2$–$C_8$alkynylsulfinyl; $C_2$–$C_8$alkynylsulfonyl; or is a group —O—CO—$R_{11}$, —O—CO—O—$R_{11}$ or —O—CO—CO—O—$R_{11}$ wherein $R_{11}$ is $C_1$–$C_4$-alkyl; or p1 Z is hydroxy; $C_1$–$C_8$alkoxy, $C_2$–$C_8$alkenyloxy, $C_2$–$C_8$alkynyloxy, $C_1$–$C_8$alkoxy-$C_1$–$C_8$alkoxy, $C_2$–$C_8$alkenyloxy-$C_1$–$C_8$alkoxy, $C_2$–$C_8$alkynyloxy-$C_1$–$C_8$alkoxy, $C_1$–$C_8$haloalkoxy, $C_3$–$C_8$cycloalkyl-$C_1$–$C_8$alkoxy, $C_1$–$C_8$alkylthio, $C_2$–$C_8$alkenylthio, $C_2$–$C_8$alkynylthio, $C_1$–$C_8$haloalkylthio, $C_3$–$C_8$cycloalkyl-$C_1$–$C_8$alkylthio or —O—CO—$C_1$–$C_4$-alkyl; or Z is hydroxy; $C_1$–$C_8$alkoxy, $C_2$–$C_8$alkenyloxy, $C_2$–$C_8$alkynyloxy, $C_1$–$C_4$alkoxy-$C_1$–$C_2$alkoxy, $C_1$–$C_8$alkylthio, $C_2$–$C_8$alkenylthio, $C_2$–$C_8$alkynylthio or —O—CO—$C_1$–$C_4$-alkyl; or Z is $C_1$–$C_8$alkoxy, $C_2$–$C_6$alkenyloxy, $C_2$–$C_6$alkynyloxy or acetoxy.

Within the various subgroups of Z those are preferred wherein the linking oxygen or sulfur bridge is an ether or thioether bridge, not the alcohol member of ester group. The same preference is observed among the various subgroup hereafter.

One preferred subgroup of the compounds of formula I consists of those compounds wherein $R_9$ is hydrogen and Z is $C_1$–$C_8$alkoxy, $C_2$–$C_6$alkenyloxy, $C_2$–$C_6$alkynyloxy or acetoxy.

Further preferred subgroups are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and $R_4$ is alkyl; and $R_{10}$ is aryl or heteroaryl, each optionally substituted by substituents selected from to group comprising alkyl, alkenyl, alkynyl, cycloalkyl, cycloalkylalkyl, phenyl and phenylalkyl, where all these groups may be substituted by one or several halogens; alkoxy; alkenyloxy; alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl and alkynyloxycarbonyl; and Z is $C_1$–$C_8$alkoxy, $C_2$–$C_6$alkenyloxy, $C_2$–$C_6$alkynyloxy or acetoxy; or $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_2$, $R_3$, $R_5$, $R_6$, and $R_7$ are hydrogen; $R_4$ is $C_{1-C6}$alkyl; $R_8$ is hydrogen or $C_1$–$C_6$alkyl; and $R_{10}$ is phenyl, naphthyl, 1,3-biphenyl or 1,4-biphenyl, each optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_9$ is hydrogen or $C_1$–$C_4$alkyl; and Z is $C_1$–$C_8$alkoxy, $C_2$–$C_6$alkenyloxy, $C_2$–$C_6$alkynyloxy or acetoxy; or $R_1$ is hydrogen, $C_1$–$C_8$alkyl, phenyl optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and $R_2$, $R_3$, $R_5$, $R_6$, and $R_7$ are hydrogen; $R_4$ is methyl or ethyl; $R_8$ is hydrogen or methyl; and $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; $R_9$ is hydrogen and Z is $C_1$–$C_8$alkoxy, $C_2$–$C_6$alkenyloxy, $C_2$–$C_6$alkynyloxy or acetoxy.

Other preferred subgroups of the compounds of formula I are those wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and $R_2$ and $R_3$ are independently of each other hydrogen or $C_1$–$C_4$alkyl; and $R_4$ is $C_1$–$C_8$alkyl, $C_2$–$C_8$alkenyl, or $C_2$–$C_8$alkynyl; and $R_5$, $R_6$, $R_7$ and $R_8$ are independently of each other hydrogen or $C_1$–$C_4$alkyl; and $R_9$ is hydrogen, $C_1$–$C_4$alkyl, $C_1$–$C_4$haloalkyl, $C_3$–$C_4$alkenyl or $C_3$–$C_4$alkynyl; and $R_{10}$ is aryl or heteroaryl, each optionally substituted with substituents selected from to group comprising alkyl, alkenyl, alkynyl, cycloalkyl, cycloalkyl-alkyl, phenyl and phenylalkyl, where all these groups may be substituted with one or more substituents selected from the group comprising halogen; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl and alkynyloxycarbonyl; and Z is hydroxy, optionally substituted aryloxy or arylthio wherein in each the aryl may be optionally substituted by one or more substituents selected from the group comprising halogen, $C_1$–$C_8$alkoxy, $C_2$–$C_8$alkenyloxy, $C_2$–$C_8$alkynyloxy, $C_1$–$C_8$alkoxy-$C_1$–$C_8$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, di-$C_1$–$C_8$alkylamino, carboxyl and $C_1$–$C_8$alkoxycarbonyl; or is optionally substituted $C_1$–$C_8$alkoxy, optionally substituted $C_2$–$C_8$alkenyloxy, optionally substituted $C_2$–$C_8$alkynyloxy, optionally substituted $C_1$–$C_8$alkylthio, optionally substituted $C_2$–$C_8$alkenylthio, optionally substituted $C_2$–$C_8$alkynylthio, optionally substituted $C_1$–$C_8$alkylsulfinyl, optionally substituted $C_2$–$C_8$alkenylsulfinyl, optionally substituted $C_2$–$C_8$alkynylsulfinyl, optionally substituted $C_1$–$C_8$alkylsulfonyl, optionally substituted $C_2$–$C_8$alkenylsulfonyl; optionally substituted $C_2$–$C_8$alkynylsulfonyl wherein each alkyl, alkenyl or alkynyl group may carry one or more substituents selected from the group comprising halogen, $C_1$–$C_4$alkyl, $C_1$–$C_4$alkoxy, $C_1$–$C_4$alkylthio, $C_3$–$C_6$cycloalkyl, nitro, cyano, hydroxy, phenyl, mercapto, $C_1$–$C_4$alkylcarbonyl and $C_1$–$C_4$alkoxycarbonyl; or is a group —O—CO—$R_{11}$, —O—CO—O—R$_{11}$ or —O—CO—CO—O—R$_{11}$
wherein R$_{11}$ is hydrogen, C$_1$–C$_4$-alkyl or C$_3$–C$_6$-cycloalkyl; or wherein R$_1$ is hydrogen, C$_1$–C$_8$alkyl, C$_3$–C$_8$cycloalkyl, phenyl or naphthyl; phenyl and naphthyl being optionally substituted by one to three substituents selected from the group comprising C$_1$–C$_8$alkyl, C$_2$–C$_8$alkenyl, C$_2$–C$_8$alkynyl, C$_1$–C$_8$haloalkyl, C$_1$–C$_8$alkoxy, C$_1$–C$_8$haloalkoxy, C$_1$–C$_8$alkylthio, C$_1$–C$_8$haloalkylthio, C$_1$–C$_8$alkylsulfonyl, halogen, cyano, nitro and C$_1$–C$_8$alkoxycarbonyl; and R$_2$ and R$_3$ are hydrogen; and R$_4$ is C$_1$–C$_6$alkyl; and R$_5$, R$_6$ and R$_7$ are hydrogen and R$_8$ is hydrogen, methyl or ethyl, preferably hydrogen or methyl; and R$_9$ is hydrogen or C$_1$–C$_4$alkyl; and R$_{q10}$ is phenyl, naphthyl or biphenyl, each optionally substituted by one to three substituents selected from the group comprising C$_1$–C$_8$alkyl, C$_2$–C$_8$alkenyl, C$_2$–C$_8$alkynyl, C$_1$–C$_8$haloalkyl, C$_1$–C$_8$alkoxy, C$_1$–C$_8$haloalkoxy, C$_1$–C$_8$alkylthio, C$_1$–C$_8$haloalkylthio, C$_1$–C$_8$alkylsulfonyl, halogen, cyano, nitro and C$_1$–C$_8$alkoxycarbonyl; and Z is hydroxy; C$_1$–C$_8$alkoxy, C$_2$–C$_8$alkenyloxy, C$_2$–C$_8$alkynyloxy, C$_1$–C$_8$alkoxy-C$_1$–C$_8$alkoxy, C$_2$–C$_8$alkenyloxy-C$_1$–C$_8$alkoxy, C$_2$–C$_8$alkynyloxy-C$_1$–C$_8$alkoxy, C$_1$–C$_8$haloalkoxy, C$_3$–C$_8$cycloalkyl-C$_1$–C$_8$alkoxy, C$_1$–C$_8$alkylthio, C$_2$–C$_8$alkenylthio, C$_2$–C$_8$alkynylthio, C$_1$–C$_8$haloalkylthio, C$_3$–C$_8$cycloalkyl-C$_1$–C$_8$alkylthio or —O—CO—C$_1$–C$_4$-alkyl; or wherein R$_1$ is hydrogen, C$_1$–C$_8$alkyl or phenyl optionally substituted by one to three substituents selected from the group comprising C$_1$–C$_8$alkyl, C$_1$–C$_8$haloalkyl, C$_1$–C$_8$alkoxy, C$_1$–C$_8$haloalkoxy, C$_1$–C$_8$alkylthio, C$_1$–C$_8$haloalkylthio, halogen, cyano, nitro and C$_1$–C$_8$alkoxycarbonyl; and R$_2$ and R$_3$ are hydrogen; and R$_4$ is C$_1$–C$_4$alkyl, and R$_5$, R$_6$ and R$_7$ are hydrogen and R$_8$ is hydrogen or methyl; and R$_9$ is hydrogen; and R$_{10}$ is phenyl, naphthyl, 1,3-biphenyl or 1,4-biphenyl, each optionally substituted by one to three substituents selected from the group comprising C$_1$–C$_8$alkyl, C$_1$–C$_8$haloalkyl, C$_1$–C$_8$alkoxy, C$_1$–C$_8$haloalkoxy, C$_1$–C$_8$alkylthio, C$_1$–C$_8$haloalkylthio, halogen, cyano, nitro and C$_1$–C$_8$alkoxycarbonyl; and Z is hydroxy; C$_1$–C$_8$alkoxy, C$_2$–C$_8$alkenyloxy, C$_2$–C$_8$alkynyloxy, C$_1$–C$_4$alkoxy-C$_1$–C$_2$alkoxy, C$_1$–C$_8$alkylthio, C$_2$–C$_8$alkenylthio, C$_2$–C$_8$alkynylthio or —O—CO—C$_1$–C$_4$-alkyl; or wherein R$_1$ is hydrogen, C$_1$–C$_8$alkyl or C$_3$–C$_8$cycloalkyl; and R$_2$, R$_3$, R$_5$, R$_6$, R$_7$, R$_8$ and R$_9$ are hydrogen; and R$_4$ is methyl or ethyl; and R$_{10}$ is phenyl, naphthyl, 1,3-biphenyl or 1,4-biphenyl, each optionally substituted by one to three substituents selected from the group comprising C$_1$–C$_8$alkyl, C$_1$–C$_8$haloalkyl, C$_1$–C$_8$alkoxy, C$_1$–C$_8$haloalkoxy, C$_1$–C$_8$alkylthio, C$_1$–C$_8$haloalkylthio, halogen, cyano, nitro and C$_1$–C$_8$alkoxycarbonyl; and Z is C$_1$–C$_8$alkoxy, C$_2$–C$_6$alkenyloxy, C$_2$–C$_6$alkynyloxy or acetoxy.

Preferred individual compounds are:

2-(4-bromo-phenyl)-2-hydroxy-N-[2-(3-methoxy-4-prop-2-ynyloxy-phenyl)-ethyl]-thioacetamide, 2-(4-chloro-phenyl)-2-hydroxy-N-[2-(3-methoxy-4-prop-2-ynyloxy-phenyl)-ethyl]-thioacetamide, 2-(3,4-dichloro-phenyl)-2-hydroxy-N-[2-(3-methoxy-4-prop-2-ynyloxy-phenyl)-ethyl]-thioacetamide 2-hydroxy-2-(4-tolyl)-N-[2-(3-methoxy-4-prop-2-ynyloxy-phenyl)-ethyl]-thioacetamide, 2-(4-ethyl-phenyl)-2-hydroxy-N-[2-(3-methoxy-4-prop-2-ynyloxy-phenyl)-ethyl]-thioacetamide, 2-(4-fluoro-phenyl)-2-hydroxy-N-[2-(3-methoxy-4-prop-2-ynyloxy-phenyl)-ethyl]-thioacetamide, 2-acetoxy-2-(4-bromo-phenyl)-N-[2-(3-methoxy-4-prop-2-ynyloxy-phenyl)-ethyl]-thioacetamide, 2-acetoxy-2-(4-chloro-phenyl)-N-[2-(3-methoxy-4-prop-2-ynyloxy-phenyl)-ethyl]-thioacetamide, 2-acetoxy-2-(3,4-dichloro-phenyl)-N-[2-(3-methoxy-4-prop-2-ynyloxy-phenyl)-ethyl]-thioacetamide, 2-acetoxy-2-(4-tolyl)-N-[2-(3-methoxy-4-prop-2-ynyloxy-phenyl)-ethyl]-thioacetamide, 2-acetoxy-2-(4-ethyl-phenyl)-N-[2-(3-methoxy-4-prop-2-ynyloxy-phenyl)-ethyl]-thioacetamide, 2-acetoxy-2-(4-fluoro-phenyl)-N-[2-(3-methoxy-4-prop-2-ynyloxy-phenyl)-ethyl]-thioacetamide, 2-(4-bromo-phenyl)-2-methoxy-N-[2-(3-methoxy-4-prop-2-ynyloxy-phenyl)-ethyl]-thioacetamide, 2-(4-chloro-phenyl)-2-methoxy-N-[2-(3-methoxy-4-prop-2-ynyloxy-phenyl)-ethyl]-thioacetamide, 2-(3,4-dichloro-phenyl)-2-methoxy-N-[2-(3-methoxy-4-prop-2-ynyloxy-phenyl)-ethyl]-thioacetamide, 2-methoxy-2-(4-tolyl)-N-[2-(3-methoxy-4-prop-2-ynyloxy-phenyl)-ethyl]-thioacetamide, 2-(4-ethyl-phenyl)-2-methoxy-N-[2-(3-methoxy-4-prop-2-ynyloxy-phenyl)-ethyl]-thioacetamide, 2-(4-fluoro-phenyl)-2-methoxy-N-[2-(3-methoxy-4-prop-2-ynyloxy-phenyl)-ethyl]-thioacetamide, 2-(4-bromo-phenyl)-2-ethoxy-N-[2-(3-methoxy-4-prop-2-ynyloxy-phenyl)-ethyl]-thioacetamide, 2-(4-chloro-phenyl)-2-ethoxy-N-[2-(3-methoxy-4-prop-2-ynyloxy-phenyl)-ethyl]-thioacetamide, 2-(3,4-dichloro-phenyl)-2-ethoxy-N-[2-(3-methoxy-4-prop-2-ynyloxy-phenyl)-ethyl]-thioacetamide, 2-ethoxy-2-(4-tolyl)-N-[2-(3-methoxy-4-prop-2-ynyloxy-phenyl)-ethyl]-thioacetamide, 2-(4-ethyl-phenyl)-2-ethoxy-N-[2-(3-methoxy-4-prop-2-ynyloxy-phenyl)-ethyl]-thioacetamide, 2-(4-fluoro-phenyl)-2-ethoxy-N-[2-(3-methoxy-4-prop-2-ynyloxy-phenyl)-ethyl]-thioacetamide, 2-(4-bromo-phenyl)-N-[2-(3-methoxy-4-prop-2-ynyloxy-phenyl)-ethyl]-2-(prop-2-ynyloxy)-thioacetamide, 2-(4-chloro-phenyl)-N-[2-(3-methoxy-4-prop-2-ynyloxy-phenyl)-ethyl]-2-(prop-2-ynyloxy)-thioacetamide, 2-(3,4-dichloro-phenyl)-N-[2-(3-methoxy-4-prop-2-ynyloxy-phenyl)-ethyl]-2-(prop-2-ynyloxy)-thioacetamide, 2-(4-tolyl)-N-[2-(3-methoxy-4-prop-2-ynyloxy-phenyl)-ethyl]-2-(prop-2-ynyloxy) -thioacetamide, 2-(4-ethyl-phenyl)-N-[2-(3-methoxy-4-prop-2-ynyloxy-phenyl)-ethyl]-2-(prop-2-ynyloxy)-thioacetamide, 2-(4-fluoro-phenyl)-N-[2-(3-methoxy-4-prop-2-ynyloxy-phenyl)-ethyl]-2-(prop-2-ynyloxy)-thioacetamide, 2-(4-bromo-phenyl)-N-[2-(3-methoxy4-pent-2-ynyloxy-phenyl)-ethyl]-2-(prop-2-ynyloxy)-thioacetamide, 2-(4-chloro-phenyl)-N-[2-(3-methoxy-4-pent-2-ynyloxy-phenyl)-ethyl]-2-(prop-2-ynyloxy)-thioacetamide, 2-(3,4-dichloro-phenyl)-N-[2-(3-methoxy-4-pent-2-ynyloxy-phenyl)-ethyl]-2-(prop-2-ynyloxy)-thioacetamide, 2-(4-tolyl)-N-[2-(3-methoxy-4-pent-2-ynyloxy-phenyl)-ethyl]-2-(prop-2-ynyloxy) -thioacetamide, 2-(4-ethyl-phenyl)-N-[2-(3-methoxy-4-pent-2-ynyloxy-phenyl)-ethyl]-2-(prop-2-ynyloxy)-thioacetamide, 2-(4-fluoro-phenyl)-N-[2-(3-methoxy-4-pent-2-ynyloxy-phenyl)-ethyl]-2-(prop-2-ynyloxy)-thioacetamide, 2-(4-bromo-phenyl)-N-[2-(3-methoxy-4-prop-2-ynyloxy-phenyl)-ethyl]-2-(pent-2-ynyloxy)-thioacetamide, 2-(4-chloro-phenyl)-N-[2-(3-methoxy-4-prop-2-ynyloxy-phenyl)-ethyl]-2-(pent-2-ynyloxy)-thioacetamide, 2-(3,4-dichloro-phenyl)-N-[2-(3-methoxy-4-prop-2-ynyloxy-phenyl)-ethyl]-2-(pent-2-ynyloxy)-thioacetamide, 2-(4-tolyl)-N-[2-(3-methoxy-4-prop-2-ynyloxy-phenyl)-ethyl]-2-(pent-2-ynyloxy)-thioacetamide, 2-(4-ethyl-phenyl)-N-[2-(3-methoxy-4-prop-2-ynyloxy-phenyl)-ethyl]-2-(pent-2-ynyloxy)-thioacetamide and 2-(4-fluoro-phenyl)-N-[2-(3-methoxy-4-prop-2-ynyloxy-phenyl)-ethyl]-2-(pent-2-ynyloxy)-thioacetamide.

Certain acetic acid derivatives have been proposed for controlling plant-destructive fungi (for example in WO 96/17840 and in WO 01/87822). The action of those preparations is not, however, satisfactory in all aspects of agricultural needs. Surprisingly, with the compound structure of formula I, new kinds of microbiocides having a high level of activity have been found.

The novel N-phenethyl thioacetic acid amide derivatives of formula I and of the subformulae Ia and Ib may be obtained according to the processes of Schemes 1 or 2, employing as starting materials of formula VI the known analogous N-phenethyl acetic acid amide derivatives as described in WO 01/87822:

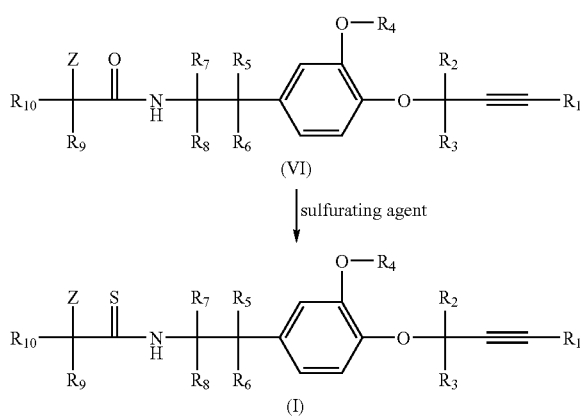

A N-phenethyl thioacetic acid amide derivative of formula I as defined above may be obtained by reacting the analogous N-phenethyl acetic acid amide derivative of formula II wherein $R_1$, $R_2$, $R_3$, $R_4$, $R_5$, $R_6$, $R_7$, $R_8$, $R_9$, $R_{10}$ and Z are as defined for formula I with a sulfurating agent, like a phosphorus sulfur compound, e.g. phosphorus pentasulfide or 2,4-bis(4-methoxyphenyl)-1,3dithia-2,4-diphosphetane-2,4-disulfide (Lawesson's reagent), in an inert diluting agent, like an inert organic solvent such as aromatic, non aromatic or halogenated hydrocarbons, e.g. benzene, toluene, xylene, chlorobenzene or chloroform, at temperatures ranging from –80° C. to +200° C., preferably at temperatures ranging from 0 to +100° C.

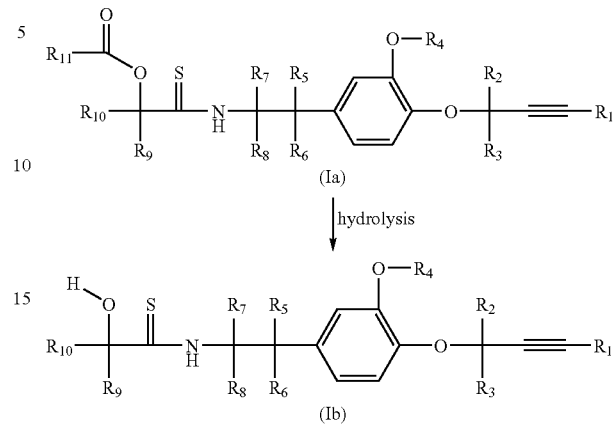

A N-phenethyl 2-hydroxythioacetic acid amide derivative of subformula Ib may be obtained by hydrolyzing the analogous N-phenethyl 2-carbonyloxy acetic acid amide derivatives of subformula Ia wherein $R_1$, $R_2$, $R_3$, $R_4$, $R_5$, $R_6$, $R_7$, $R_8$, $R_9$, $R_{10}$, $R_{11}$ and Z as defined for formula I.

The compounds of subformula Ia may be obtained according to Scheme 1 from known compounds of formula VIa which corresponds to the compounds of formula VI wherein Z is $R_{11}$—CO—O—.

The hydrolysis reaction is conducted by reaction with water in the presence of an alkaline base like a metal hydroxide or -carbonate, e.g. lithium hydroxide LiOH, sodium hydroxide NaOH, potassium hydroxide KOH, sodium carbonate $Na_2CO_3$ or potassium carbonate $K_2CO_3$ at temperatures ranging from –40° C. to the reflux temperature of the reaction mixture, preferentially ranging from 0° C. to +60° C. The hydrolysis reaction is with advantage performed in an inert diluting medium, like an organic solvent which is freely miscible with water, such as an ether, e.g. tetrahydrofuran or dioxane, such as a ketone, e.g. acetone or ethylmethylketone, such as an alcohol, e.g. methanol or ethanol, or excess water or in a mixture of these diluting agents.

Starting materials of formula VI may be synthesized according to Schemes A, B, C, D and E wherein $R_1$, $R_2$, $R_3$, $R_4$, $R_5$, $R_6$, $R_7$, $R_8$, $R_9$, $R_{10}$, $R_{11}$ and Z are as defined for formula I, $R_{12}$ is alkyl, alkenyl or alkynyl, R' and R" independently of each other are lower alkyl such as methyl, ethyl, propyl, isopropyl, butyl or isobutyl, Hal is halogen, preferably chlorine or bromine and Y is a leaving group like a halide such as a chloride or bromide or a sulfonic ester such as a tosylate, mesylate or triflate.

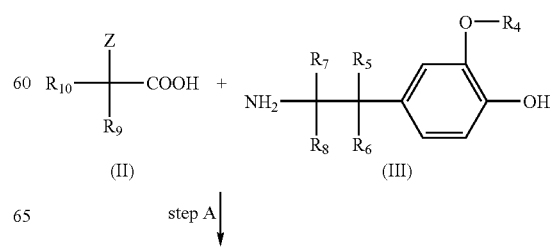

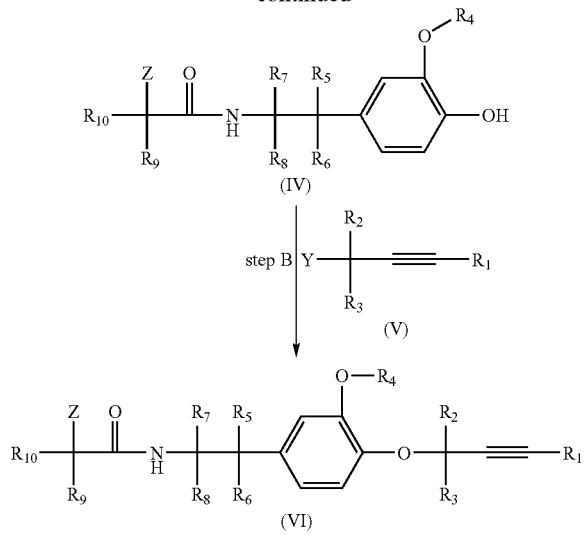

Step A: An acid of formula II or a carboxy-activated derivative of an acid of formula II wherein $R_9$, $R_{10}$ and Z are as defined for formula I is reacted with an amine of formula III wherein $R_4$, $R_5$, $R_6$, $R_7$ and $R_8$ are as defined for formula I, optionally in the presence of a base and optionally in the presence of a diluting agent.

Carboxy-activated derivatives of the acid of formula II are all compounds having an activated carboxyl group like an acid halide, such as an acid chloride, like symmetrical or mixed anhydrides, such as mixed anhydrides with O-alkylcarbonates, like activated esters, such as p-nitrophenylesters or N-hydroxysuccinimidesters, as well as in-situ-formed activated forms of the amino acid of formula II with condensating agents, such as dicyclohexylcarbodiimide, carbonyldiimidazole, benzotriazol-1-yloxy-tris(dimethylamino) phosphonium hexafluorophosphate, O-benzotriazol-1-yl N,N,N',N'-bis(pentamethylene)uronium hexafluorophosphate, O-benzotriazol-1-yl N,N,N',N'-bis(tetramethylene) uronium hexafluorophosphate, O-benzotriazol-1-yl N,N,N', N'-tetramethyluronium hexafluorophosphate or benzotriazol-1-yloxy-tripyrrolidinophosphonium hexafluorophosphate. The mixed anhydrides of the acids of the formula II may be prepared by reaction of an amino acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, N-methyl-piperidine or N-methyl-morpholine.

The present reaction is preferably performed in a solvent like aromatic, non-aromatic or halogenated hydrocarbons, such as chlorohydrocarbons e.g. dichloromethane or toluene; ketones e.g. acetone; esters e.g. ethyl acetate; amides e.g. N,N-dimethylformamide; nitrites e.g. acetonitrile; or ethers e.g. diethylether, tert-butyl-methylether, dioxane or tetrahydrofuran or water. It is also possible to use mixtures of these solvents. The reaction is performed optionally in the presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from −80° C. to +150° C., preferentially at temperatures ranging from −40° C. to +40° C.

Step B: The compounds of formula VI may then finally be prepared by reacting a phenol of formula IV wherein $R_4$, $R_5$, $R_6$, $R_7$, $R_8$, $R_9$, $R_{10}$ and Z are as defined for formula I with a compound of formula V wherein $R_1$, $R_2$ and $R_3$ are as defined for formula I and wherein Y is a leaving group like a halide such as a chloride or bromide or a sulfonic ester such as a tosylate, mesylate or triflate.

The reaction is advantageously performed in a solvent like aromatic, non-aromatic or halogenated hydrocarbons, such as chlorohydrocarbons e.g. dichloromethane or toluene; ketones e.g. acetone or 2-butanone; esters e.g. ethyl acetate; ethers e.g. diethylether, tert-butyl-methylether, dioxane or tetrahydrofuran, amides e.g. dimethylformamide, nitrites e.g. aceto-nitrile, alcohols e.g. methanol, ethanol, isopropanol, n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

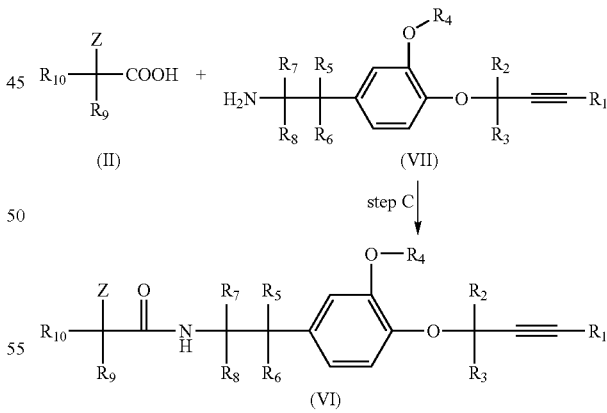

Scheme B

Step C: Alternatively to step A and step B, an acid of formula II or a carboxy-activated derivative of an acid of formula II wherein $R_9$, $R_{10}$ and Z are as defined for formula I is reacted with an amine of formula VII wherein $R_1$, $R_2$, $R_3$, $R_4$, Rs $R_6$, $R_7$ and $R_8$ are as defined for formula I under the same conditions as defined for step A, optionally in the presence of a base and optionally in the presence of a diluting agent.

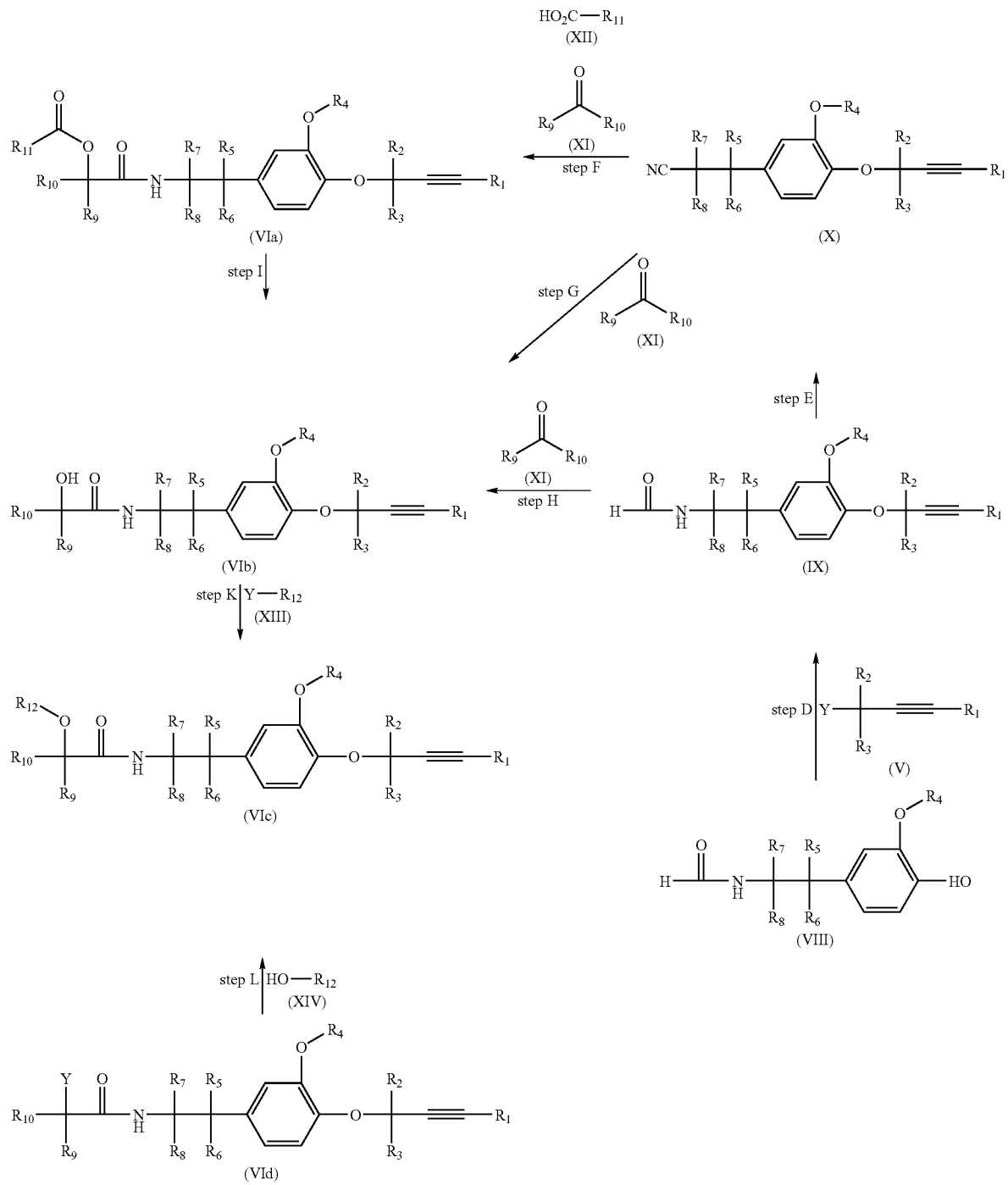

Scheme C

Step D: A compound of formula VIII wherein $R_4$, $R_5$, $R_6$, $R_7$ and $R_8$ are as defined for formula I is alkylated with a compound of formula V (see Scheme 1) wherein $R_1$, $R_2$, $R_3$ and Y are as defined for Scheme 1 under the same conditions as defined for step B in Scheme 1.

Step E: A compound of formula IX wherein $R_1$, $R_2$, $R_3$, $R_4$, $R_5$, $R_6$, $R_7$ and $R_8$ are as defined for formula I is dehydrated to an isocyanide of formula X wherein $R_1$, $R_2$, $R_3$, $R_4$, $R_5$, $R_6$, $R_7$ and $R_8$ are as defined for formula I under conditions known per se (D. Seebach, G. Adam, T. Gees, M. Schiess, W. Weigang, *Chem. Ber.* 1988, 121, 507).

Step F: An isocyanide of formula X wherein $R_1$, $R_2$, $R_3$, $R_4$, $R_5$, $R_6$, $R_7$ and $R_8$ are as defined for formula I is reacted in a three-component Passerini reaction (J. March, *Advanced Organic Chemistry*, 4th ed., Wiley, 1992, p. 980) with an aldehyde or ketone of formula XI, wherein $R_9$ and $R_{10}$ are as defined for formula I in the presence of a carboxylic acid XII wherein $R_{11}$ is hydrogen or lower alkyl, typically acetic acid, to give a O-acyl-α-hydroxy amide of formula VIa, wherein $R_1, R_2, R_3, R_4, R_5, R_6, R_7, R_8, R_9$ and $R_{10}$ are as defined for formula I.

Step G: Alternatively to step F, an isocyanide of formula X wherein $R_1, R_2, R_3, R_4, R_5, R_6, R_7$ and $R_8$ are as defined for formula I is reacted with an aldehyde or ketone of formula XI in the presence of titanium tetrachloride to give an α-hydroxy amide of the formula VIb (where $R_1, R_2, R_3, R_4, R_5, R_6, R_7, R_8, R_9$ and $R_{10}$ have the same meaning as defined above) under conditions known per se (D. Seebach, G. Adam, T. Gees, M. Schiess, W. Weigang, *Chem. Ber.* 1988, 121, 507; O. Ort, U. Döller, W. Reissel, S. D. Lindell, T. L. Hough, D. J. Simpson, J. P. Chung, *Pesticide Sci.* 1997, 50, 331).

Step H: Alternatively to step F and step G, a compound of formula IX, wherein $R_1, R_2, R_3, R_4, R_5, R_6, R_7$ and $R_8$ are halide such as a chloride or bromide or a sulfonic ester such as a tosylate, mesylate or triflate to a compound of formula Ia wherein $R_1, R_2, R_3, R_4, R_5, R_6, R_7, R_8, R_9$ and $R_{10}$ are as defined for formula I and $R_{12}$ is alkyl, alkenyl or alkynyl under the same conditions as defined for step B in Scheme 1.

Step L: An α-substituted amide of formula VId wherein $R_1, R_2, R_3, R_4, R_5, R_6, R_7, R_8, R_9$ and $R_{10}$ are as defined for formula I and Y is a leaving group like a halide such as a chloride or bromide or a sulfonic ester such as a tosylate, mesylate or triflate, is reacted with a compound XIV wherein $R_{12}$ is alkyl, alkenyl or alkynyl to a compound of formula Ia wherein $R_1, R_2, R_3, R_4, R_5, R_6, R_7, R_8, R_9$ and $R_{10}$ are as defined for formula I and $R_{12}$ is alkyl, alkenyl or alkynyl under the same conditions as defined for step B in Scheme 1.

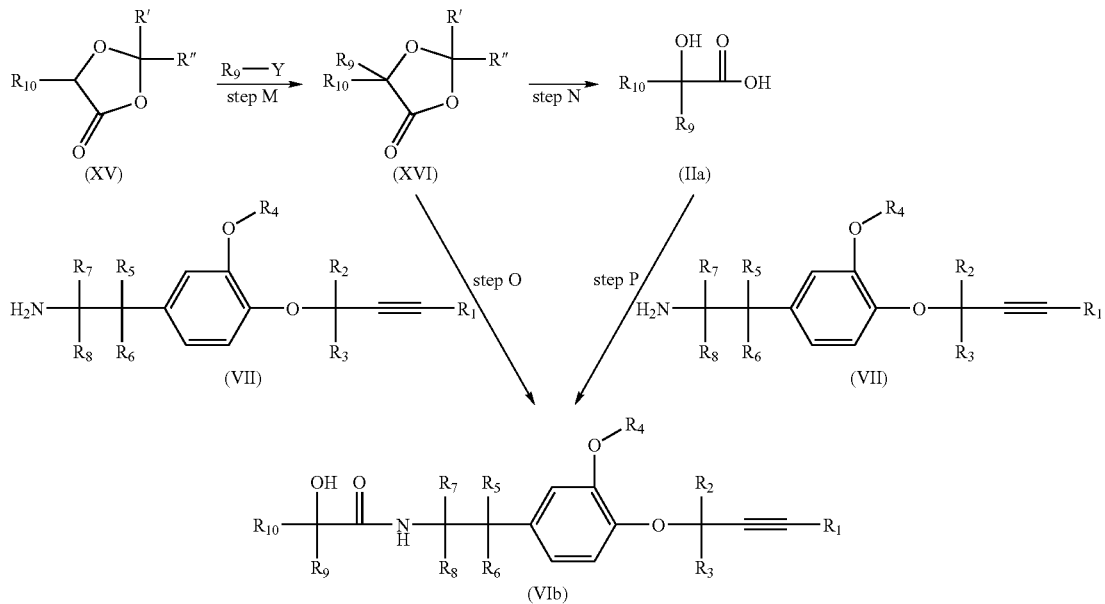

Scheme D as defined for formula I is treated with one phosgene equivalent (e.g. triphosgene) and a base (e.g. triethylamine) and in a second step, without isolation of the isocyanide intermediate, is further treated with titanium tetrachloride and an aldehyde or ketone of formula XI, wherein $R_9$ and $R_{10}$ as defined for formula I under conditions known per se (WO 96/17840) to give an α-hydroxy amide of the formula VIb, wherein $R_1, R_2, R_3, R_4, R_5, R_6, R_7, R_8, R_9$ and $R_{10}$ are as defined for formula I.

Step I: An O-acyl-α-hydroxy amide of formula VIa wherein $R_1, R_2, R_3, R_4, R_5, R_6, R_7, R_8, R_9, R_{10}$ and $R_{11}$ are as defined above is hydrolyzed to a an α-hydroxy amide of formula VIb, wherein $R_1, R_2, R_3, R_4, R_5, R_6, R_7, R_8, R_9$ and $R_{10}$ are as defined for formula I under classical conditions (J. March, *Advanced Organic Chemistry*, 4th ed., Wiley, 1992).

Step K: An α-hydroxy amide of formula VIb wherein $R_1, R_2, R_3, R_4, R_5, R_6, R_7, R_8, R_9$ and $R_{10}$ are as defined for formula I is reacted with a compound XIII wherein $R_{12}$ is alkyl, alkenyl or alkynyl and Y is a leaving group like a Step M: A dioxolanone XV (obtained by the condensation of a mandelic acid with a ketone R'—CO—R" under acid catalysis (see EP-A-071568) is subsequently treated with a base such as lithium diisopropylamide (LDA) and an alkylating agent $R_9$—Y wherein $R_9$ is alkyl and Y is a leaving group like a halide such as a chloride or bromide or a sulfonic ester such as a tosylate, mesylate or triflate, according to known procedures (F. Cavelier, S. Gomez, R. Jacquier, J. Verducci, *Tetrahedron Lett.* 1994, 2891, DE 4319887).

Steps N, O and P: The resulting dioxolanone XVI is either heated with the appropriate amine VII at temperatures in between +50° C. to +200° C. (step O), or the dioxolanone is first hydrolysed in aqueous diluted mineral acid (e.g. HCl) or under basic conditions (aqueous sodium hydroxide (0–120° C.; step N) to the substituted hydroxy acid IIa which then can be amidated (step P, according to step A, scheme 1). Hydroxy acids IIa can also be obtained by reaction of a Grignard reagent $R_{10}$-MgHal (starting from an aryl-halide and Mg) with an appropriate α-keto acid ester (A. F. Hegarty, P. O'Neill, *Synthesis* 1993, 606).
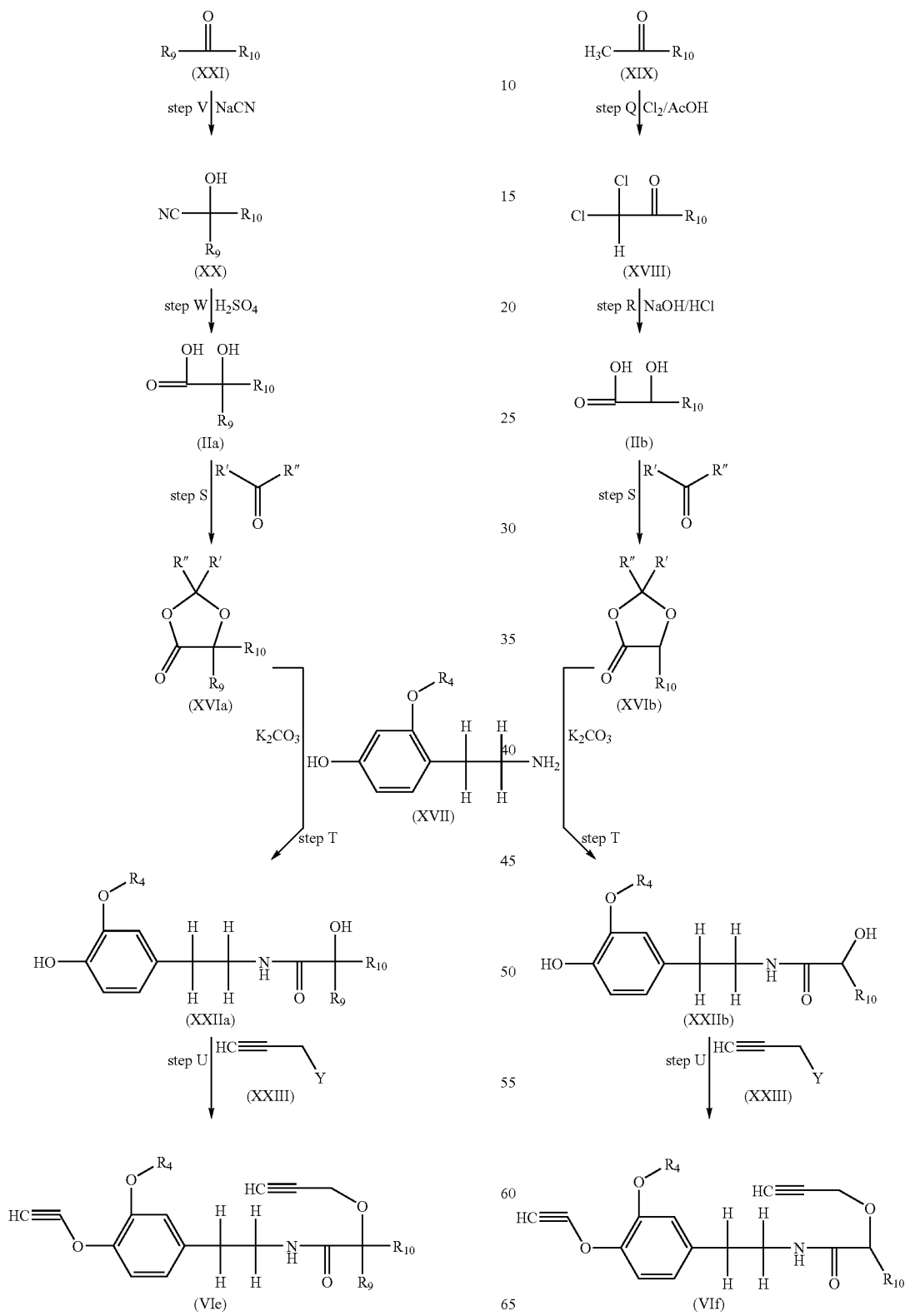
Scheme E Step Q: A ketone of formula XIX, wherein $R_{10}$ is as defined for formula I, is chlorinated to give a dichloroketone of formula XVIII, wherein $R_{10}$ is as defined for formula I, under conditions known per se (J. G. Aston, J. D. Newkirk, D. M. Jenkins, J. Dorsky, Org. Synth. Coll. Vol. 3, 1955, 538).

Step R: A dichloroketone of formula XVIII, wherein $R_{10}$ is as defined for formula I, is reacted with an inorganic base such as sodium hydroxide or potassium hydroxide to give a α-hydroxy acid of formula IIb, wherein $R_{10}$ is as defined for formula I, under conditions known per se (J. G. Aston, J. D. Newkirk, D. M. Jenkins, J. Dorsky, Org. Synth. Coll. Vol. 3, 1955, 538).

Step S: A α-hydroxy acid of formula IIa or IIb, wherein $R_9$ and $R_{10}$ is as defined for formula I is reacted with a mineral acid such as sulfuric acid, hydrochloric acid or nitric acid and a ketone R'—CO—R", wherein R' and R" are alkyl to give the dioxolanones XVIa ad XVIb, wherein $R_9$ and $R_{10}$ are as defined for formula I and R' and R" are alkyl.

Step T: A dioxolanone of formula XVIa or XVIb, wherein $R_9$ and $R_{10}$ are as defined for formula I and R' and R" are alkyl is reacted with an amine of formula XVII, wherein $R_4$ is as defined for formula I in the presence of a base, such as triethylamine, N,N-diisopropyl-ethylamine, pyridine, N-methyl-piperidine, N-methyl-morpholine, potassium carbonate or sodium carbonate at temperatures ranging from −80° C. to +200° C., preferentially at temperatures ranging from 0° C. to 120° C. to give a compound of formulae XXIIa or XXIIb, wherein $R_4$, $R_9$ and $R_{10}$ are as defined for formula I.

Step U: A compound of formula XXIIa or XXIIb, wherein $R_4$, $R_9$ and $R_{10}$ are as defined for formula I, is reacted with a compound of formula XXIII, wherein Y is a leaving group like a halide such as chlorine or bromine or a sulfonic ester group such as a tosylate, mesylate or triflate, under phase-transfer alkylation conditions in the presence of an inorganic base such as sodium hydroxide or potassium hydroxide and a phase-transfer catalyst like benzyltriethylammonium chloride or tetrabutylammonium bromide to obtain a compound of formula VIe or VIf, wherein $R_4$, $R_9$ and $R_{10}$ are as defined for formula I.

Step V: An ketone of formula XXI, wherein $R_9$ and $R_{10}$ is as defined for formula I, is reacted with an inorganic cyanide, like sodium cyanide or potassium cyanide, in the presence of an inorganic sulfite, such as sodium bisulfite or potassium bisulfite to obtain a cyanohydrin of formula XX, wherein $R_9$ and $R_{10}$ is as defined for formula I, under conditions known per se (B. B. Corson, R. A. Dodge, S. A. Harris, J. S. Yeaw, Org. Synth. Coll. Vol. 1, 1941, 336).

Step W: A cyanohydrin of formula XX, wherein $R_9$ and $R_{10}$ is as defined for formula I, is reacted with a mineral acid, such as sulfuric acid, hydrochloric acid or nitric acid to yield a α-hydroxy acid of formula IIa , wherein $R_9$ and $R_{10}$ is as defined for formula I, under conditions known per se (B. B. Corson, R. A. Dodge, S. A. Harris, J. S. Yeaw, Org. Synth. Coll. Vol. 1, 1941, 336).

The compounds of formula I are oils or solids at room temperature and are distinguished by valuable microbiocidal properties. They can be used in the agricultural sector or related fields preventatively and curatively in the control of plant-destructive microorganisms. The compounds of formula I according to the invention are distinguished at low rates of concentration not only by outstanding microbiocidal, especially fungicidal, activity but also by being especially well tolerated by plants.

Surprisingly, it has now been found that the compounds of formula I have for practical purposes a very advantageous microbiocidal spectrum in the control of phytopathogenic microorganisms, especially fungi. They possess very advantageous curative and preventative properties and are used in the protection of numerous crop plants. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infecfions and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilizers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities. Such mixtures are not limited to two active Ingredients (one of formula I and one of the list of other fungicides), but to the contrary many comprise more than one active ingredient of the component of formula I and more than one other fungicide. Mixing components which are particularly suited for this purpose include e.g. azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; HEC 5725 (proposed common name fluoxastrobin), orysastrobin (proposed common name), dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofosmethyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph or flumorlin), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, DPX-KQ 926 (proposed comon name proquinazid), JAU 6476 (proposed common name prothioconazole), IKF–916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilizers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilizers or other active ingredients for obtaining special effects.

The Examples which follow illustrate the invention described above, without limiting the scope thereof in any way. Temperatures are given in degrees Celsius. Ph stands for phenyl.

PREPARATION EXAMPLES

Example 1.1

2-(4-Chloro-phenyl)-N-[2-(3-methoxy-4-prop-2-ynyloxy-phenyl)-ethyl]-2-(prop-2-ynyloxy)-thioacetamide

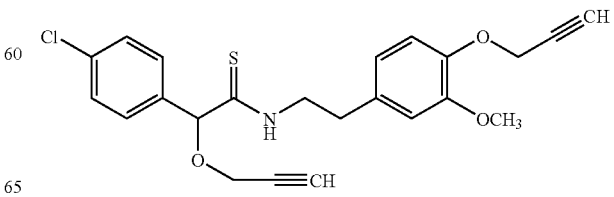

2-(4-Chloro-phenyl)-N-[2-(3-methoxy-4-prop-2-ynyloxy-phenyl)-ethyl]-2-(prop-2-ynyloxy)-acetamide (0.822 g) and benzene (30 ml) are stirred at +55° C. 2,4-bis-(4-methoxyphenyl)-1,3-dithia-2,4-diphosphetane-2,4-disulfide ("Lawesson's reagent"; 1.61 g) is added. The reaction mixture is stirred for additional 7 hours at +55° C. to +60° C. After cooling to room temperature diethylether (100 ml) is added. The mixture is then filtered. The solvent of the filtrate is evaporated. 2-(4-Chloro-phenyl)-N-[2-(3-methoxy-4-prop-2-ynyloxy-phenyl)-ethyl]-2-(prop-2-ynyloxy)-thioacetamide is obtained which is purified by flash-column-chromatography on silica gel using ethyl acetate/hexane. The purified product is in form of a resin. $^1$H-NMR (300 MHz, CDCl$_3$, δ(ppm)): 2.45–2.55(m, 2H), 2.95(t, 2H), 3.85 (s, 3H), 3.9–4.2(m, 4H), 4.75(d, 2H), 5.35(s, 1H), 6.65–6.8 (m, 2H), 7.0(d, 1H), 7.2–7.4(m, 4H), 8.4–8.6(m, 1H).

According to example 1.1. the compounds listed in table 1 are obtained.

TABLE A1

| No. | R$_1$ | R$_8$ | R$_9$ | R$_{10}$ | Z | physic.-chem. data |
|---|---|---|---|---|---|---|
| A1.01 | H | H | H | 4-Cl-Ph | O—CH$_2$—C≡CH | resin, $^1$H-NMR (300 MHz, CDCl$_3$, δ(ppm)) : 2.45–2.55(m,2H), 2.95(t,2H), 3.85(s,3H), 3.9–4.2(m,4H), 4.75(d,2H), 5.35 (s,1H), 6.65–6.8(m,2H), 7.0 (d,1H), 7.2–7.4(m,4H), 8.4–8.6 (m,1H) |
| A1.02 | H | H | H | 4-Br-Ph | O—CH$_2$—C≡CH | resin, $^1$H-NMR (300 MHz, CDCl$_3$, δ(ppm)) 2.4–2.6 (m,2H), 2.95(t,2H), 3.85(s,3H), 3.8–4.2(m,4H), 4.8(d,2H), 5.35 (s,1H), 6.65–6.8(m,2H), 7.0 (d,1H), 7.2(d,2H), 7.45(d,2H), 8.4–8.6(m,1H) |
| A1.03 | H | H | H | 4-Cl-Ph | O—CO—CH$_3$ | resin, $^1$H-NMR (300 MHz, CDCl$_3$, δ(ppm)) : 2.05(s,3H), 2.5 (t,1H), 2.95(t,2H), 3.85(s,3H), 3.9–4.1(m,2H), 4.25(d,2H), 6.4 (s,1H), 6.65–6.8(m,2H), 7.0 (s,1H), 7.25–7.35(m,4H), 8.4–8.55(m,1H) |
| A1.04 | H | H | H | 4-Br-Ph | O—CO—CH$_3$ | resin, $^1$H-NMR (300 MHz, CDCl$_3$, δ(ppm)) : 2.05(s,3H), 2.5 (t,1H), 2.95(t,2H), 3.85(s,3H), 3.9–4.05(m,2H), 4.3(d,2H), 6.4 (s,1H), 6.65–6.8(m,2H), 7.0 (d,1 H), 7.2(d,2H), 7.45(d,2H), 8.4–8.55(m,1H) |
| A1.05 | H | H | H | 4-(4-Cl-Ph)-Ph | O—CH$_2$—C≡CH | resin, $^1$H-NMR (300 MHz, CDCl$_3$, δ(ppm)) : 2.45–2.55(m, 2H), 2.9(t,2H), 3.75(s,3H), 3.8–4.2(m,4H), 4.7(d,2H), 5.35 (s,1H), 6.65–6.75(m,2H), 6.9 (d,1H), 7.2–7.5(m,8H), 8.4–8.55 (m,1H) |
| A1.06 | H | H | H | 4-(4-Br-Ph)-Ph | O—CH$_2$—C≡CH | resin, $^1$H-NMR (300 MHz, CDCl$_3$, δ(ppm)) 2.3–2.45 (m,2H), 2.85(t,2H), 3.7(s,3H), 3.75–4.1(m,4H), 4.6(d,2H), 5.25 (s,1H), 6.5–6.65(m,2H), 6.8 (d,1H), 7.1–7.45(m,8H), 8.3–8.5 (m,1H) |
| A1.07 | H | H | H | 4-(4-H$_3$C-Ph)-Ph | O—CH$_2$—C≡CH | resin, $^1$H-NMR (300 MHz, CDCl$_3$, δ(ppm)) 2.4(s,3H), 2.45–2.55(m,1H), 3.0(t,2H), 3.85 (s,3H), 3.9–4.25(m,4H), 4.8 (d,2H), 5.4(s,1H), 6.7–6.8 (m,2H), 7.0(d,1H), 7.25(d,2H), 7.35(d,2H), 7.45(d,2H), 7.55 (d,2H), 8.5–8.65(m,1H) |

Example 2.1.

2-(4-Chloro-phenyl)-2-hydroxy-N-[2-(3-methoxy-4-prop-2-ynyloxy-phenyl)-ethyl]-thioacetamide

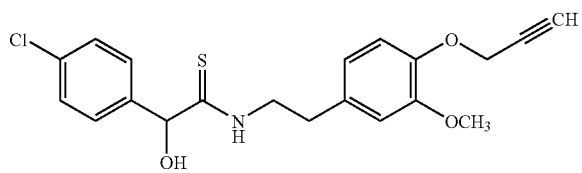

A mixture of 2-acetoxy-2-(4-chloro-phenyl)-N-[2-(3-methoxy-4-prop-2-ynyloxy-phenyl)-ethyl]-thioacetamide (compound A1.03; 0.603 g), sodium hydroxide (1.4 ml 1 n solution in water) and methanol (5 ml) is stirred for 6 hours at room temperature. Water (30 ml) is added. The reaction mixture is extracted with ethyl acetate (2×100 ml). The organic layers are washed with brine (20 ml), dried and the solvent is evaporated. 2-(4-Chloro-phenyl)-2-hydroxy-N-[2-(3-methoxy-4-prop-2-ynyloxy-phenyl)-ethyl]-thioacetamide is obtained which is purified by flash-column-chromatography on silica gel using ethyl acetate/hexane, yielding a resin, $^1$H-NMR (300 MHz, CDCl$_3$, δ(ppm)): 2.5(t, 1H), 2.9(t, 2H), 3.8(s, 3H), 3.85–4.05(m, 2H), 4.25 (s, 1H), 4.75(d, 2H), 5.1(s, 1H), 6.5(dd, 1H), 6.65(d, 1H), 6.9(d, 1H), 7.2(d, 2H), 7.3(d, 2H), 7.7–7.8(m, 1H).

According to example 2.1. the compounds listed in table A2 are obtained.

TABLE A2

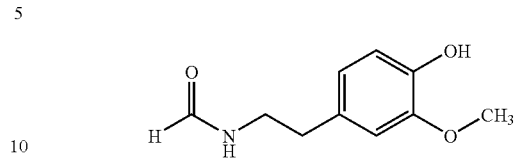

a) N-[2-(4-Hydroxy-3-methoxy-phenyl)-ethyl]-formamide

Formic acid (230 g, 5.0 mol) is added dropwise to acetic anhydride (383 g, 3.75 mol) at 0° C. This mixture is stirred for 2 hours at +55° C. and subsequently cooled again to 0° C. Tetrahydrofuran (500 ml) is added at this temperature followed by 4-(2-amino-ethyl)-2-methoxy-phenol hydrochloride (50 g, 0.25 mol). The resulting white suspension is stirred for 18 hours at +75° C., changing into a yellow solution. The reaction mixture is evaporated and the residue is submitted to flash-chromatography to yield N-[2-(4-hydroxy-3-methoxy-phenyl)-ethyl]-formamide. $^1$H-NMR (300 MHz, CDCl$_3$, δ(ppm)): 2.85 (t, 2H, CH$_2$CH$_2$), 3.57 (t, 2H, CH$_2$CH$_2$), 3.82 (s, 3H, OCH$_3$), 5.69 (bs, 1H, NH), 6.67–7.09 (m, 3H, CH arom.), 8.12 (s, 1H, CHO).

| No. | R$_1$ | R$_8$ | R$_9$ | R$_{10}$ | physic. -chem. data |
|---|---|---|---|---|---|
| A2.01 | H | H | H | 4-Cl-Ph | resin, $^1$H-NMR (300 MHz, CDCl$_3$, δ(ppm)) : 2.5(t,1H), 2.9 (t,2H), 3.8(s,3H), 3.85–4.05(m,2H) 4.25(s,1H), 4.75(d,2H), 5.1(s,1H), 6.5(dd,1H), 6.65(d,1H), 6.9(d,1H), 7.2(d,2H), 7.3 (d,2H), 7.7–7.8(m,1H) |
| A2.02 | H | H | H | 4-Br-Ph | resin, $^1$H-NMR (300 MHz, CDCl$_3$, δ(ppm)) : 2.5(t,1H), 2.9 (t,2H), 3.85(s,3H), 3.9–4.25(m,3H), 4.8(d,2H), 5.1(s,1H), 6.5 (dd,1H), 6.7(d,1H), 6.9(d,1H), 7.15(d,2H), 7.45(d,2H), 7.6–7.75(m,1H) |

Example 3.1.

Preparation of the Starting Material 2-(4-chlorophenyl)-N-[2-(3-methoxy-4-prop-2-ynyloxy-phenyl)-ethyl]-2-(prop-2-ynyloxy)-acetamide

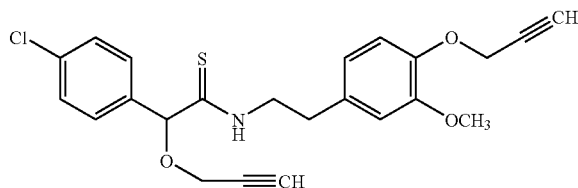

b) N-[2-(3-Methoxy-4-prop-2-ynyloxy-phenyl)-ethyl]-formamide

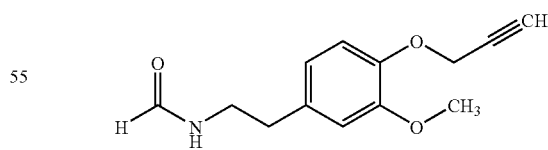

Sodium methoxide (32 ml of a 5.4 M solution in methanol, 0.17 mol) is added to a solution of N-[2-(4-hydroxy-3-methoxy-phenyl)-ethyl]-formamide (32 g, 0.16 mol) in methanol (400 ml). Propargyl bromide (20 g, 0.17 mol) is added and the mixture is refluxed for 4 hours. After evaporation the residue is taken up in ethyl acetate (400 ml) and washed with water (2×200 ml). The organic layer is dried over magnesium sulfate and evaporated. The residue is submitted to flash-chromatography to give the N-[2-(3-methoxy-4-prop-2-ynyloxy-phenyl)-ethyl]-formamide.
¹H-NMR (300 MHz, CDCl₃, δ(ppm)): 2.44 (t, 1H, C≡CH), 2.73 (t, 2H, CH₂CH₂), 3.51 (t, 2H, CH₂CH₂), 3.82 (s, 3H, OCH₃), 4.69 (m, 2H, OCH₂), 5.53(bs, 1H, NH), 6.62–6.95 (m, 3H, CH arom.), 8.09 (s, 1H, CHO).

c) 2-(4-Chloro-phenyl)-2-hydroxy-N-[2-(3-methoxy-4-prop-2-ynyloxy-phenyl)-ethyl]-acetamide

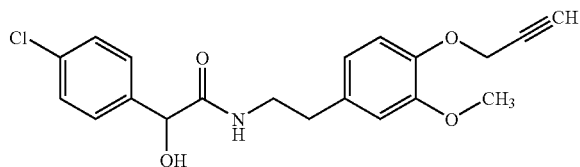

N-[2-(3-methoxy-4-prop-2-ynyloxy-phenyl)-ethyl]-formamide (34 g, 0.14 mol) and triethylamine (34 g, 0.34 mol) are dissolved in dichloromethane (120 ml). Bis(trichloromethyl) carbonate (triphosgene, 16 g, 55 mmol) in dichloromethane (80 ml) is added at +5° C. The mixture is stirred for 4 hours at +5° C. and then cooled to −78° C. A solution of titanium tetrachloride (28 g, 0.15 mol) in dichloromethane (150 ml) is added and the mixture is stirred for 2 hours at −40° C. 4-Chlorobenzaldehyde (20 g, 0.14 mol) in dichloromethane (70 ml) is added dropwise and the mixture is stirred for 17 hours at room temperature. The mixture is hydrolyzed with 5N HCl (80 ml), stirred 30 minutes at room temperature and washed with water. After evaporation of the organic layer the residue is submitted to flash-chromatography (ethyl acetate/hexane) to give 2-(4-chloro-phenyl)-2-hydroxy-N-[2-(3-methoxy-4-prop-2-ynyloxy -phenyl)-ethyl]-acetamide. ¹H-NMR (300 MHz, CDCl₃, δ(ppm)): 2.54 (t, 1H, CO≡CH), 2.72 (t, 2H, CH₂CH₂), 3.53 (t, 2H, CH₂CH₂), 3.84 (s, 3H, OCH₃), 4.78 (m, 2H, OCH₂), 4.98 (s, 1H, CHOH), 6.07 (bs, 1H, NH), 6.53–7.38 (m, 7H, CH arom.

d) 2-(4-Chloro-phenyl)-2-hydroxy-N-[2-(3-methoxy-4-prop-2-ynyloxy-phenyl)-ethyl]-acetamide (2.6 g, 7.0 mmol) is dissolved in N,N-dimethylformamide (30 ml). Sodium hydride (0.18 g, 7.5 mmol) is added in portions at +5° C. The mixture is stirred for 30 minutes at room temperature. Subsequently iodomethane (1.1 g, 7.5 mmol) is added dropwise and the resulting mixture is stirred for 3 more hours at room temperature. The reaction mixture is poured on ice/water (200 ml) and extracted with ethyl acetate (2×200 ml). The combined organic layer is washed with brine (200 ml) and dried over magnesium sulfate. After evaporation of the solvent, the residue is purified by chromatography (ethyl acetate/hexane) to yield 2-(4-chloro-phenyl)-2-methoxy-N-[2-(3-methoxy-4-prop-2-ynyloxy-phenyl)-ethyl]-acetamide.
¹H-NMR (300 MHz, CDCl₃, δ(ppm)): 2.53 (t, 1H, C≡CH), 2.80 (t, 2H, CH₂CH₂), 3.34 (s, 2H, OCH₃), 3.55 (t, 2H, CH₂CH₂), 3.84 (s, 3H, OCH₃), 4.58 (s, 1H, CHOH), 4.79 (m, 2H, OCH₂), 6.68–7.34 (m, 8H, CH arom., NH).

According to example 3.1. the compounds listed in table A3 are obtained

TABLE A3

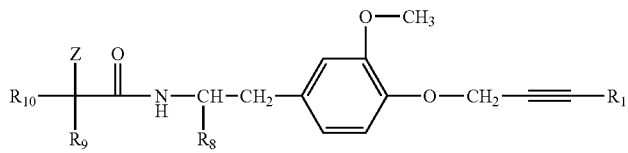

| No. | R₁ | R₈ | R₉ | R₁₀ | Z | m.p. ¹H-NMR (300 MHz, CDCl₃: δ(ppm) |
|---|---|---|---|---|---|---|
| A3.01 | H | H | H | 4-Cl-Ph | O—CH₂—C≡CH | m.p. 90–92° C. |
| A3.02 | H | H | H | 4-Br-Ph | O—CH₂—C≡CH | m.p. 92–94° C. |
| A3.03 | H | H | H | 4-(4-Cl-Ph)-Ph | O—CH₂—C≡CH | m.p. 96–97° C. |
| A3.04 | H | H | H | 4-(4-Br-Ph)-Ph | O—CH₂—C≡CH | m.p. 94–95° C. |
| A3.05 | H | H | H | 4-(4-H₃C-Ph)-Ph | O—CH₂—C≡CH | m.p. 104–105° C. |
| A3.06 | H | H | H | 3-Br-Ph | O—CH₂—C≡CH | 2.42(t,2H), 2.72(t,2H), 3.47(t,2H), 3.78(s,3H), 3.91 (dd,1H), 4.12 (dd,1H), 4.70(d,2H), 4.89 (s,1H), 6.60–7.44(m,7H) |
| A3.07 | H | H | H | 3-H₃C-Ph | O—CH₂—CH₃ | 1.20(t,3H), 2.36(s,3H), 2.53(t,1H), 2.82(t,2H), 3.41–3.58(m,4H), 3.85(s, 3H), 4.68(s,1H), 4.78(d, 2H), 6.72–7.28(m,7H) |
| A3.08 | H | H | H | 4-Cl-Ph | —O—CH₂C(CH₃)=CH₂ | 1.69(s,3H), 2.53(t,1H), 2.80(t,2H), 3.53(t,2H), 3.86(s,3H), 4.69–4.92(m, 5H), 6.69–7.33(m,7H) |
| A3.09 | H | H | H | 4-Br-Ph | —O—CH₂C≡CCH₂CH₃ | 1.05(t,3H), 2.14(dt,2H), 2.44(t,1H), 2.70(t,2H), 3.42(t,2H), 3.73(s,3H), 3.86(dd,1H), 4.09 (dd,1H), 4.68(d,2H), 4.88 (s,1H), 6.58–7.42(m,7H) |

Example 4.1.

2-Acetoxy-2-(4-chloro-phenyl)-N-[2-(3-methoxy-4-prop-2-ynyloxy-phenyl)-ethyl]-acetamide

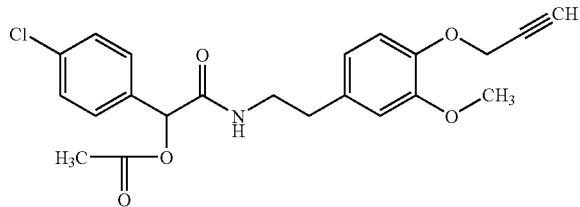

Acetylchloride (0.7 g, 8.9 mmol) is slowly added to a cooled (0° C.) mixture of 2-(4-chloro-phenyl)-2-hydroxy-N-[2-(3-methoxy-4-prop-2-ynyloxy-phenyl)-ethyl]-acetamide (3.0 g, 8.0 mmol) and pyridine (0.7 g, 8.9 mmol) in 30 ml of dichloromethane. The reaction mixture is stirred for 2 hours at room temperature and subsequently poured on ice and extracted with ethyl acetate. The combined organic extracts are washed with brine, dried over sodium sulfate and the solvent is evaporated, the residue is purified by chromatography on silica gel to give 2-acetoxy-2-(4-chloro-phenyl)-N-[2-(3-methoxy-4-prop-2-ynyloxy-phenyl)-ethyl]-acetamide. $^1$H-NMR (300 MHz, CDCl$_3$): 2.13 (s, 3H, CH$_3$CO$_2$), 2.52 (t, 1H, C≡CH), 2.80 (t, 2H, CH$_2$CH$_2$), 3.57 (t, 2H, CH$_2$CH$_2$), 3.87 (s, 3H, OCH$_3$), 4.79 (d, 2H, OCH$_2$C≡C), 6.03 (s, 1H, CHOH), 6.65–7.34 (m, 8H, CH arom., NH).

According to example 4.1. the compounds listed in table A4 are obtained

TABLE A4

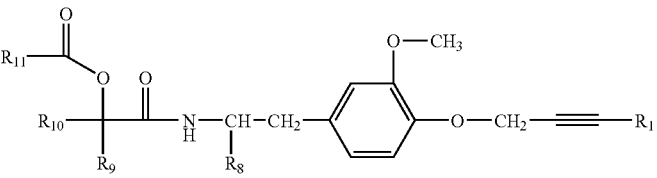

| No. | R$_1$ | R$_8$ | R$_9$ | R$_{10}$ | R$_{11}$ | physic-chem. data |
|---|---|---|---|---|---|---|
| A4.01 | H | H | H | 4-Cl-Ph | CH$_3$ | resin |
| A4.02 | H | H | H | 4-Cl-Ph | CH$_2$CH$_3$ | resin |
| A4.03 | H | H | H | 4-Cl-Ph | CH$_2$CN | resin |
| A4.04 | H | H | H | 4-Cl-Ph | C≡CH | resin |
| A4.05 | H | H | H | 4-Cl-Ph | C(CH$_3$)$_3$ | resin |
| A4.06 | H | H | H | 4-Cl-Ph | C(CH$_3$)=CH$_2$ | resin |
| A4.07 | H | H | H | 4-Cl-Ph | CH$_2$OCH$_3$ | resin |
| A4.08 | H | H | H | 4-Cl-Ph | CO$_2$CH$_3$ | m.p. 52° C. |
| A4.09 | H | H | H | 4-Cl-Ph | CO$_2$CH$_2$CH$_3$ | m.p. 49° C. |
| A4.10 | H | H | H | 4-Cl-Ph | C(=O)N(CH$_2$CH$_3$)$_2$ | resin |
| A4.11 | H | H | H | 4-Cl-Ph | CH$_2$CO$_2$CH$_3$ | resin |
| A4.12 | H | H | H | 4-Cl-Ph | Ph | m.p. 53° C. |
| A4.13 | H | H | H | 4-Cl-Ph | OCH$_3$ | resin |
| A4.14 | H | H | H | 4-Br-Ph | CO$_2$CH$_3$ | resin |
| A4.15 | H | H | H | 4-Br-Ph | CO$_2$CH$_2$CH$_3$ | m.p. 49° C. |
| A4.16 | H | H | H | 3,4-Cl$_2$-Ph | CO$_2$CH$_3$ | m.p. 88° C. |
| A4.17 | H | H | H | 4-C$_2$H$_5$-Ph | CO$_2$CH$_3$ | resin |
| A4.18 | H | H | H | 4-H$_3$C-Ph | CO$_2$CH$_3$ | resin |
| A4.19 | H | H | H | 4-F$_3$C-Ph | CO$_2$CH$_3$ | m.p. 95° C. |
| A4.20 | H | H | H | 4-F-Ph | CO$_2$CH$_3$ | m.p. 114° C. |
| A4.21 | H | H | H | 4-Cl-3-F-Ph | CO$_2$CH$_3$ | m.p. 98° C. |

Analogously to the above examples the compounds of tables 1 to 41 are obtained.

Ph stands for phenyl

TABLE 1

Compounds represented by the Formula I.1

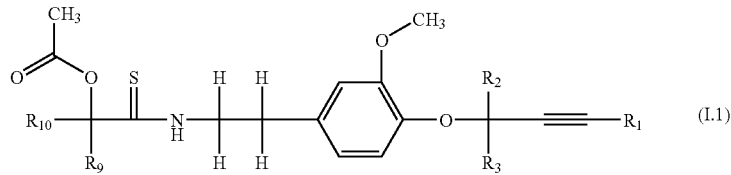

(I.1)

wherein the combination of the groups $R_1$, $R_2$, $R_3$, $R_9$ and $R_{10}$ corresponds each to one row in table A.

TABLE 2

Compounds represented by the Formula I.2

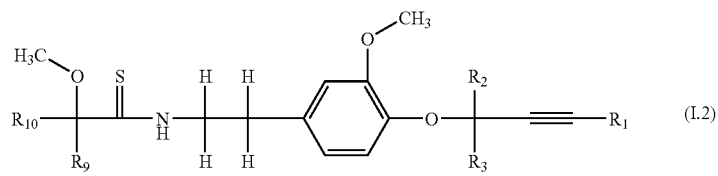

(I.2)

wherein the combination of the groups $R_1$, $R_2$, $R_3$, $R_9$ and $R_{10}$ corresponds each to one row in table A.

TABLE 3

Compounds represented by the Formula I.3

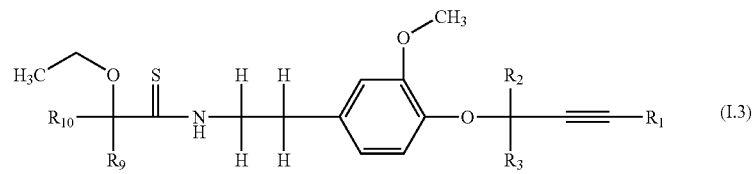

(I.3)

wherein the combination of the groups $R_1$, $R_2$, $R_3$, $R_9$ and $R_{10}$ corresponds each to one row in table A.

TABLE 4

Compounds represented by the Formula I.4

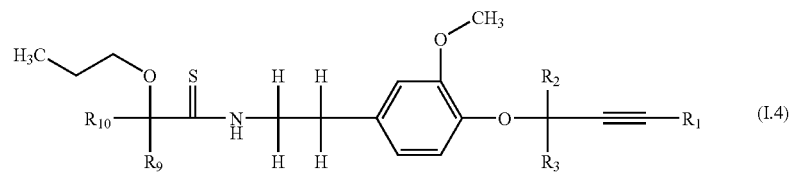

(I.4)

wherein the combination of the groups $R_1$, $R_2$, $R_3$, $R_9$ and $R_{10}$ corresponds each to one row in table A.

TABLE 5

Compounds represented by the Formula I.5

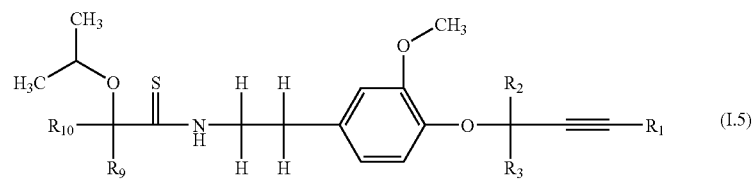

(I.5)

wherein the combination of the groups $R_1$, $R_2$, $R_3$, $R_9$ and $R_{10}$ corresponds to each one row in table A.

TABLE 6

Compounds represented by the Formula I.6

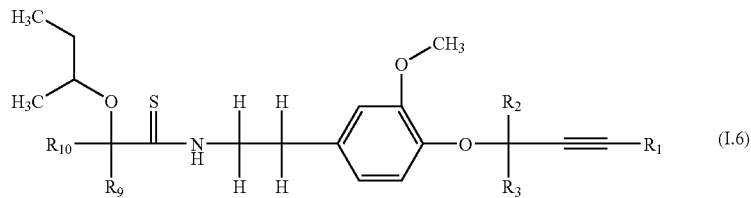

(I.6)

wherein the combination of the groups $R_1$, $R_2$, $R_3$, $R_9$ and $R_{10}$ corresponds each to one row in table A.

TABLE 7

Compounds represented by the Formula I.7

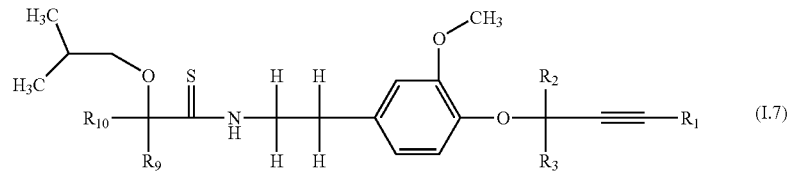

(I.7)

wherein the combination of the groups $R_1$, $R_2$, $R_3$, $R_9$ and $R_{10}$ corresponds each to one row in table A.

TABLE 8

Compounds represented by the Formula I.8

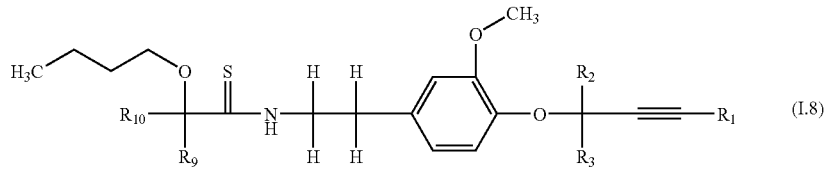

(I.8)

wherein the combination of the groups $R_1$, $R_2$, $R_3$, $R_9$ and $R_{10}$ corresponds each to one row in table A.

TABLE 9

Compounds represented by the Formula I.9

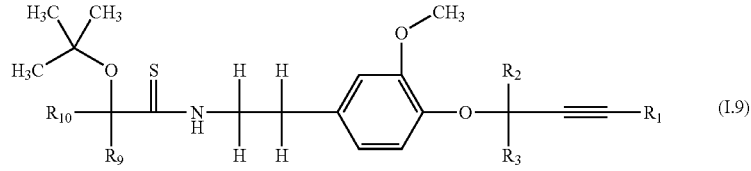

(I.9)

wherein the combination of the groups $R_1$, $R_2$, $R_3$, $R_9$ and $R_{10}$ corresponds each to one row in table A.

TABLE 10
Compounds represented by the Formula I.10

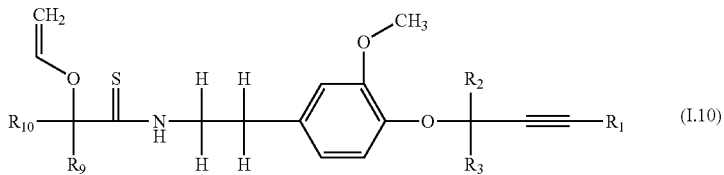
(I.10)

wherein the combination of the groups $R_1$, $R_2$, $R_3$, $R_9$ and $R_{10}$ corresponds each to one row in table A.

TABLE 11
Compounds represented by the Formula I.11

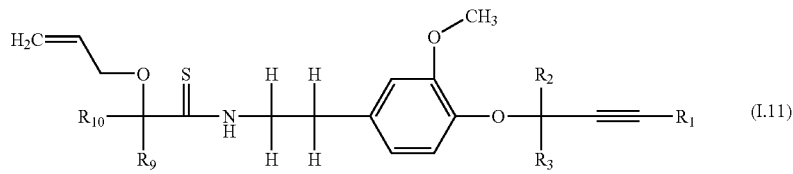
(I.11)

wherein the combination of the groups $R_1$, $R_2$, $R_3$, $R_9$ and $R_{10}$ corresponds each to one row in table A.

TABLE 12
Compounds represented by the Formula I.12

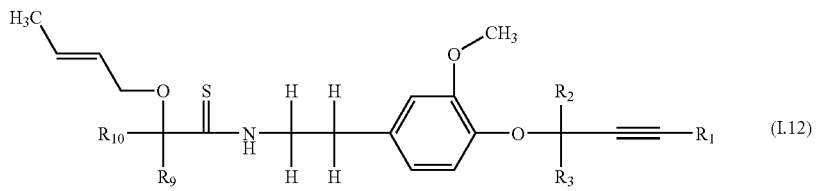
(I.12)

wherein the combination of the groups $R_1$, $R_2$, $R_3$, $R_9$ and $R_{10}$ corresponds each to one row in table A.

TABLE 13
Compounds represented by the Formula I.13

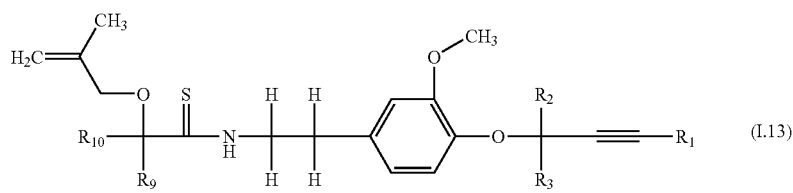
(I.13)

wherein the combination of the groups $R_1$, $R_2$, $R_3$, $R_9$ and $R_{10}$ corresponds each to one row in table A.

TABLE 14

Compounds represented by the Formula I.14

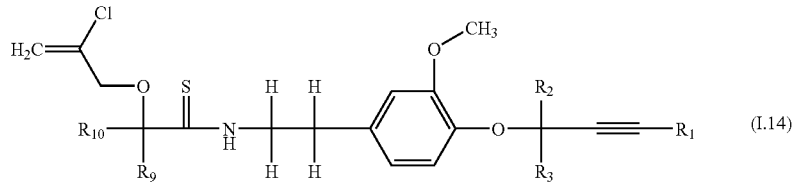

(I.14)

wherein the combination of the groups $R_1$, $R_2$, $R_3$, $R_9$ and $R_{10}$ corresponds each to one row in table A.

TABLE 15

Compounds represented by the Formula I.15

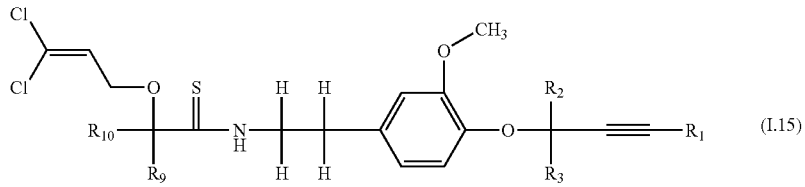

(I.15)

wherein the combination of the groups $R_1$, $R_2$, $R_3$, $R_9$ and $R_{10}$ corresponds each to one row in table A.

TABLE 16

Compounds represented by the Formula I.16

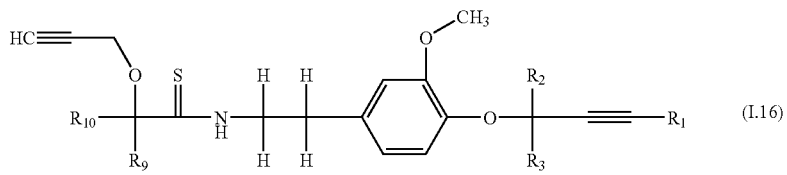

(I.16)

wherein the combination of the groups $R_1$, $R_2$, $R_3$, $R_9$ and $R_{10}$ corresponds each to one row in table A.

TABLE 17

Compounds represented by the Formula I.17

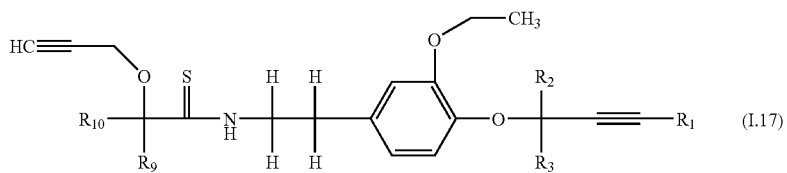

(I.17)

wherein the combination of the groups $R_1$, $R_2$, $R_3$, $R_9$ and $R_{10}$ corresponds each to one row in table A.

TABLE 18

Compounds represented by the Formula I.18

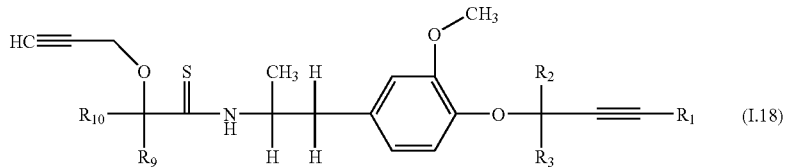 (I.18)

wherein the combination of the groups $R_1$, $R_2$, $R_3$, $R_9$ and $R_{10}$ corresponds each to one row in table A.

TABLE 19

Compounds represented by the Formula I.19

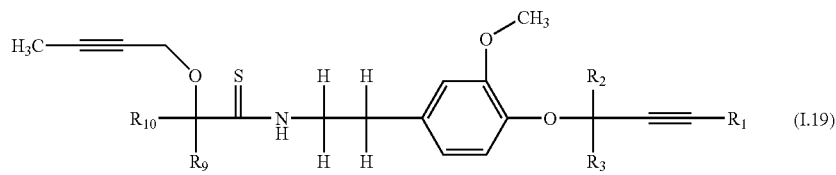 (I.19)

wherein the combination of the groups $R_1$, $R_2$, $R_3$, $R_9$ and $R_{10}$ corresponds each to one row in table A.

TABLE 20

Compounds represented by the Formula I.20

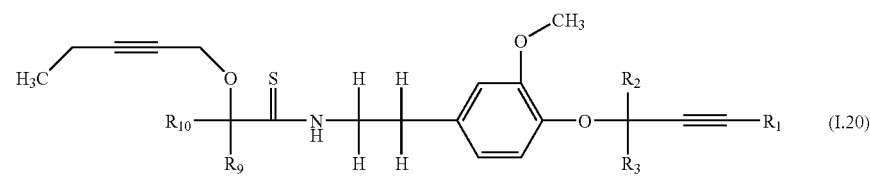 (I.20)

wherein the combination of the groups $R_1$, $R_2$, $R_3$, $R_9$ and $R_{10}$ corresponds each to one row in table A.

TABLE 21

Compounds represented by the Formula I.21

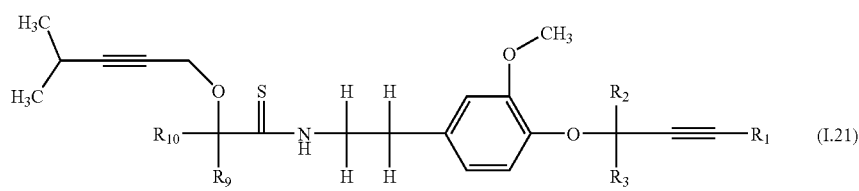 (I.21)

wherein the combination of the groups $R_1$, $R_2$, $R_3$, $R_9$ and $R_{10}$ corresponds each to one row in table A.

TABLE 22

Compounds represented by the Formula I.22

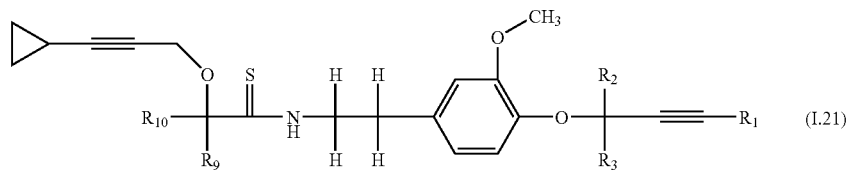 (I.21)

wherein the combination of the groups $R_1$, $R_2$, $R_3$, $R_9$ and $R_{10}$ corresponds each to one row in table A.

TABLE 23

Compounds represented by the Formula I.23

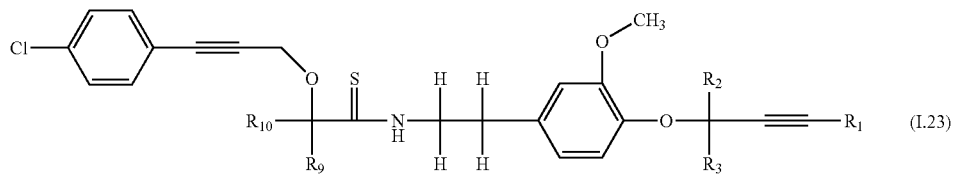 (I.23)

wherein the combination of the groups $R_1$, $R_2$, $R_3$, $R_9$ and $R_{10}$ corresponds each to one row in table A.

TABLE 24

Compounds represented by the Formula I.24

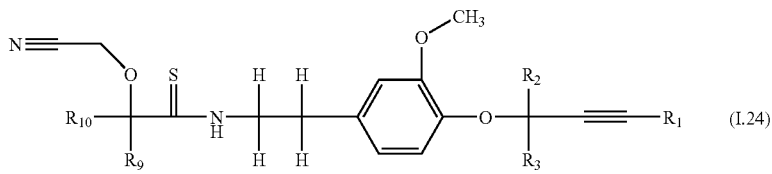 (I.24)

wherein the combination of the groups $R_1$, $R_2$, $R_3$, $R_9$ and $R_{10}$ corresponds each to one row in table A.

TABLE 25

Compounds represented by the Formula I.25

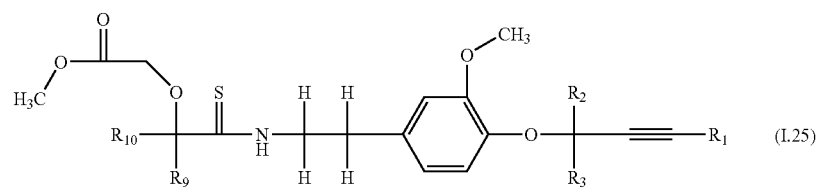 (I.25)

wherein the combination of the groups $R_1$, $R_2$, $R_3$, $R_9$ and $R_{10}$ corresponds each to one row in table A.

TABLE 26

Compounds represented by the Formula I.26

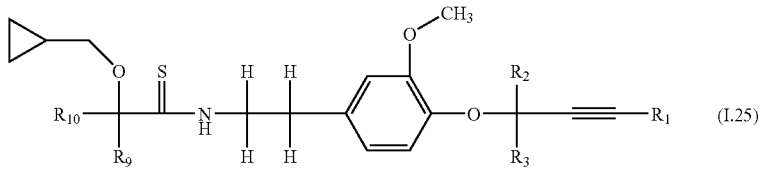
(I.25)

wherein the combination of the groups $R_1$, $R_2$, $R_3$, $R_9$ and $R_{10}$ corresponds each to one row in table A.

TABLE 27

Compounds represented by the Formula I.27

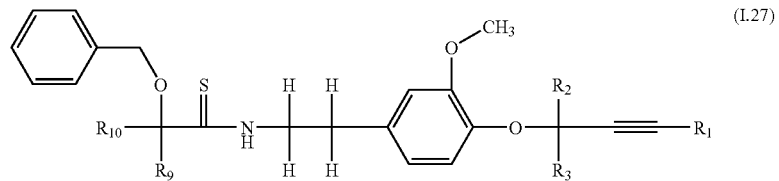
(I.27)

wherein the combination of the groups $R_1$, $R_2$, $R_3$, $R_9$ and $R_{10}$ corresponds each to one row in table A.

TABLE 28

Compounds represented by the Formula I.28

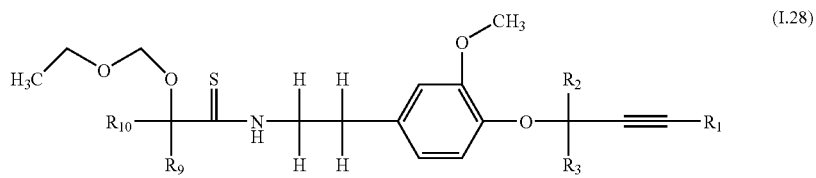
(I.28)

wherein the combination of the groups $R_1$, $R_2$, $R_3$, $R_9$ and $R_{10}$ corresponds each to one row in table A.

TABLE 29

Compounds represented by the Formula I.29

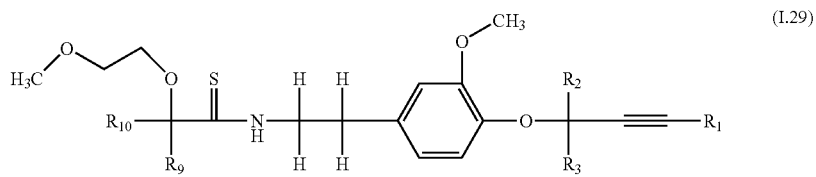
(I.29)

wherein the combination of the groups $R_1$, $R_2$, $R_3$, $R_9$ and $R_{10}$ corresponds each to one row in table A.

TABLE 30

Compounds represented by the Formula I.30

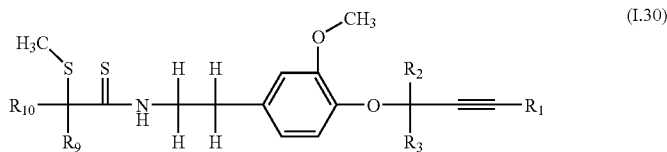
(I.30)

wherein the combination of the groups $R_1$, $R_2$, $R_3$, $R_9$ and $R_{10}$ corresponds each to one row in table A.

TABLE 31

Compounds represented by the Formula I.31

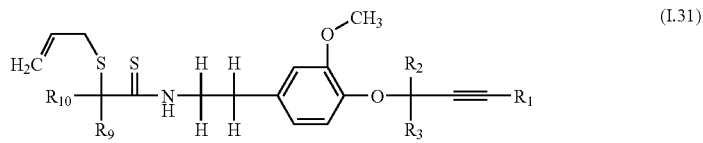
(I.31)

wherein the combination of the groups $R_1$, $R_2$, $R_3$, $R_9$ and $R_{10}$ corresponds each to one row in table A.

TABLE 32

Compounds represented by the Formula I.32

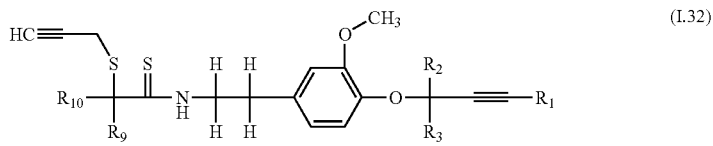
(I.32)

wherein the combination of the groups $R_1$, $R_2$, $R_3$, $R_9$ and $R_{10}$ corresponds each to one row in table A.

TABLE 33

Compounds represented by the Formula I.33

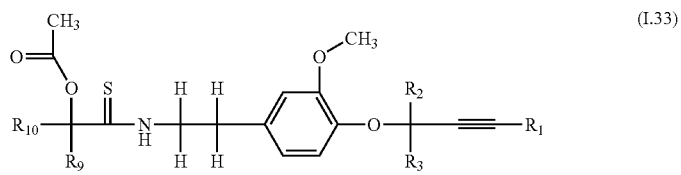
(I.33)

wherein the combination of the groups $R_1$, $R_2$, $R_3$, $R_9$ and $R_{10}$ corresponds each to one row in table A.

TABLE 34

Compounds represented by the Formula I.34

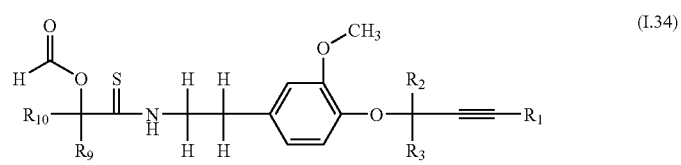
(I.34)

wherein the combination of the groups $R_1$, $R_2$, $R_3$, $R_9$ and $R_{10}$ corresponds each to one row in table A.

TABLE 35

Compounds represented by the Formula I.35

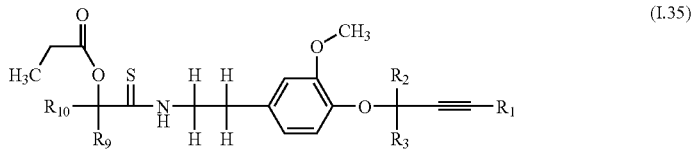

(I.35)

wherein the combination of the groups $R_1$, $R_2$, $R_3$, $R_9$ and $R_{10}$ corresponds each to one row in table A.

TABLE 36

Compounds represented by the Formula I.36

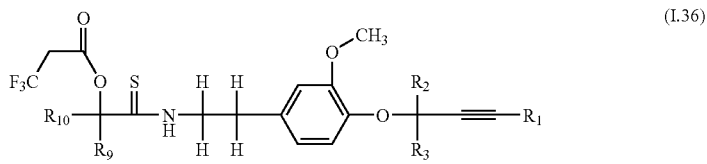

(I.36)

wherein the combination of the groups $R_1$, $R_2$, $R_3$, $R_9$ and $R_{10}$ corresponds each to one row in table A.

TABLE 37

Compounds represented by the Formula I.37

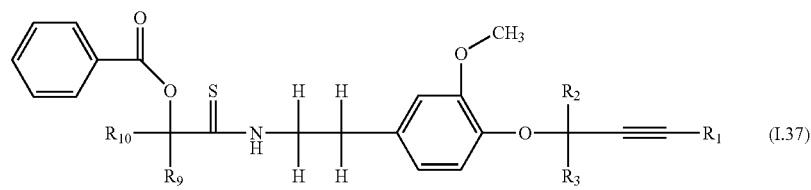

(I.37)

wherein the combination of the groups $R_1$, $R_2$, $R_3$, $R_9$ and $R_{10}$ corresponds each to one row in table A.

TABLE 38

Compounds represented by the Formula I.38

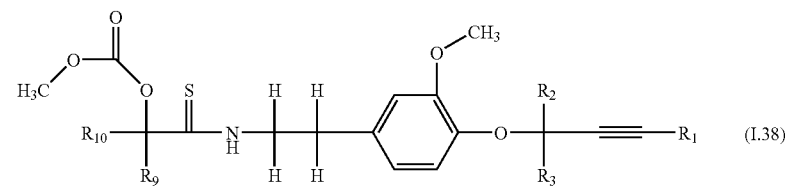

(I.38)

wherein the combination of the groups $R_1$, $R_2$, $R_3$, $R_9$ and $R_{10}$ corresponds each to one row in table A.

TABLE 39

Compounds represented by the Formula I.39

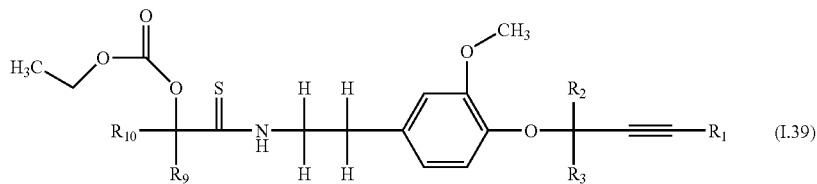 (I.39)

wherein the combination of the groups $R_1$, $R_2$, $R_3$, $R_9$ and $R_{10}$ corresponds each to one row in table A.

TABLE 40

Compounds represented by the Formula I.40

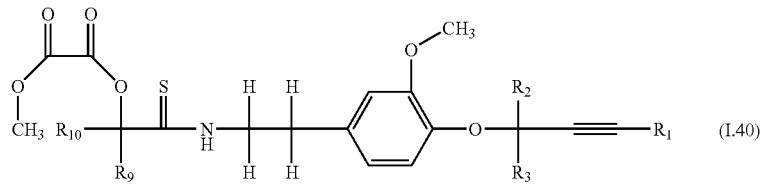 (I.40)

wherein the combination of the groups $R_1$, $R_2$, $R_3$, $R_9$ and $R_{10}$ corresponds each to one row in table A.

TABLE 41

Compounds represented by the Formula I.41

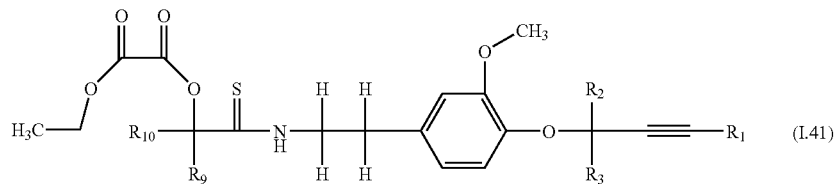 (I.41)

wherein the combination of the groups $R_1$, $R_2$, $R_3$, $R_9$ and $R_{10}$ corresponds each to one row in table A.

TABLE A

| No. | $R_1$ | $R_2$ | $R_3$ | $R_9$ | $R_{10}$ |
|-----|-------|-------|-------|-------|----------|
| 001 | H | H | H | H | Ph |
| 002 | H | H | H | H | naphthyl |
| 003 | H | H | H | H | 2-thienyl |

TABLE A-continued
| No. | R₁ | R₂ | R₃ | R₉ | R₁₀ |
|-----|----|----|----|----|-----|
| 004 | H | H | H | H | 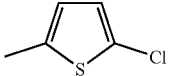 |
| 005 | H | H | H | H | 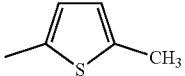 |
| 006 | H | H | H | H | 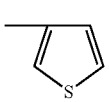 |
| 007 | H | H | H | H | 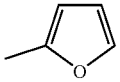 |
| 008 | H | H | H | H | 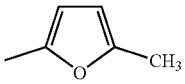 |
| 009 | H | H | H | H | 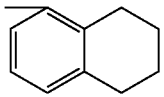 |
| 010 | H | H | H | H | 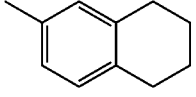 |
| 011 | H | H | H | H | 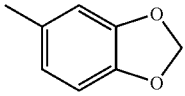 |
| 012 | H | H | H | H | 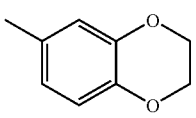 |
| 013 | H | H | H | H | 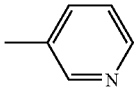 |
| 014 | H | H | H | H | 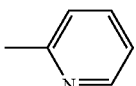 |
| 015 | H | H | H | H | 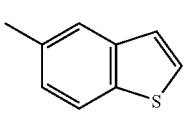 |
| 016 | H | H | H | H | 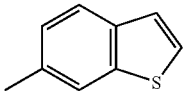 |
| 017 | H | H | H | H | 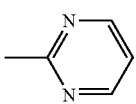 |

TABLE A-continued

| No. | R₁ | R₂ | R₃ | R₉ | R₁₀ |
|---|---|---|---|---|---|
| 018 | H | H | H | H | 4-methylpyrimidinyl (structure) |
| 019 | H | H | H | H | 3-CH₃-Ph |
| 020 | H | H | H | H | 4-H₂O=CH-Ph |
| 021 | H | H | H | H | 4-HC≡C-Ph |
| 022 | H | H | H | H | 4-CH₃—CH₂—CH₂-Ph |
| 023 | H | H | H | H | 4-(CH₃)₂CH-Ph |
| 024 | H | H | H | H | 4-(CH₃)₃C-Ph |
| 025 | H | H | H | H | 4-CH₃—CH₂O-Ph |
| 026 | H | H | H | H | 4-HC≡CO-Ph |
| 027 | H | H | H | H | 4-PhO-Ph |
| 028 | H | H | H | H | 4-CH₃S-Ph |
| 029 | H | H | H | H | 4-CF₃S-Ph |
| 030 | H | H | H | H | 4-CH₃SO₂-Ph |
| 031 | H | H | H | H | 4-CN-Ph |
| 032 | H | H | H | H | 4-NO₂-Ph |
| 033 | H | H | H | H | 4-CH₃O₂C-Ph |
| 034 | H | H | H | H | 3-Br-Ph |
| 035 | H | H | H | H | 3-Cl-Ph |
| 036 | H | H | H | H | 2-Cl-Ph |
| 037 | H | H | H | H | 2,4-Cl₂-Ph |
| 038 | H | H | H | H | 3,4,5-Cl₃-Ph |
| 039 | H | H | H | H | 3-Cl-4-F-Ph |
| 040 | H | H | H | H | 3,4-F₂-Ph |
| 041 | H | H | H | H | 3,4-Br₂-Ph |
| 042 | H | H | H | H | 3,4-(CH₃O)₂-Ph |
| 043 | H | H | H | H | 3,4-(CH₃)₂-Ph |
| 044 | H | H | H | H | 3-Cl-4-CN-Ph |
| 045 | H | H | H | H | 4-Cl-3-CN-Ph |
| 046 | H | H | H | H | 3-Br-4-CH₃-Ph |
| 047 | H | H | H | H | 4-CH₃O-3-CH₃-Ph |
| 048 | H | H | H | H | 3-F-4-CH₃O-Ph |
| 049 | H | H | H | H | 4-F-Ph |
| 050 | H | H | H | CH₃ | 4-F-Ph |
| 051 | CH₃ | H | H | H | 4-F-Ph |
| 052 | CH₂CH₃ | H | H | H | 4-F-Ph |
| 053 | C₃H₇-i | H | H | H | 4-F-Ph |
| 054 | C₃H₅-cycl | H | H | H | 4-F-Ph |
| 055 | H | H | H | H | 4-Cl-Ph |
| 056 | H | H | H | CH₃ | 4-Cl-Ph |
| 057 | CH₃ | H | H | H | 4-Cl-Ph |
| 058 | CH₂CH₃ | H | H | H | 4-Cl-Ph |
| 059 | C₃H₇-i | H | H | H | 4-Cl-Ph |
| 060 | C₃H₅-cycl | H | H | H | 4-Cl-Ph |
| 061 | H | H | H | H | 4-Br-Ph |
| 062 | H | H | H | CH₃ | 4-Br-Ph |
| 063 | CH₃ | H | H | H | 4-Br-Ph |
| 064 | CH₂CH₃ | H | H | H | 4-Br-Ph |
| 065 | C₃H₇-i | H | H | H | 4-Br-Ph |
| 066 | C₃H₅-cycl | H | H | H | 4-Br-Ph |
| 067 | H | H | H | H | 4-CH₃-Ph |
| 068 | H | H | H | CH₃ | 4-CH₃-Ph |
| 069 | CH₃ | H | H | H | 4-CH₃-Ph |
| 070 | CH₂CH₃ | H | H | H | 4-CH₃-Ph |
| 071 | C₃H₇-i | H | H | H | 4-CH₃-Ph |
| 072 | C₃H₅-cycl | H | H | H | 4-CH₃-Ph |
| 073 | H | H | H | H | 4-CH₃—CH₂-Ph |
| 074 | H | H | H | CH₃ | 4-CH₃—CH₂-Ph |
| 075 | CH₃ | H | H | H | 4-CH₃—CH₂-Ph |
| 076 | CH₂CH₃ | H | H | H | 4-CH₃—CH₂-Ph |
| 077 | C₃H₇-i | H | H | H | 4-CH₃—CH₂-Ph |
| 078 | C₃H₅-cycl | H | H | H | 4-CH₃—CH₂-Ph |
| 079 | H | H | H | H | 3,4-Cl₂-Ph |
| 080 | H | H | H | CH₃ | 3,4-Cl₂-Ph |
| 081 | CH₃ | H | H | H | 3,4-Cl₂-Ph |
| 082 | CH₂CH₃ | H | H | H | 3,4-Cl₂-Ph |
| 083 | C₃H₇-i | H | H | H | 3,4-Cl₂-Ph |
| 084 | C₃H₅-cycl | H | H | H | 3,4-Cl₂-Ph |
| 085 | H | H | H | H | 4-Cl-3-F-Ph |
| 086 | H | H | H | CH₃ | 4-Cl-3-F-Ph |
| 087 | CH₃ | H | H | H | 4-Cl-3-F-Ph |
| 088 | CH₂CH₃ | H | H | H | 4-Cl-3-F-Ph |
| 089 | C₃H₇-i | H | H | H | 4-Cl-3-F-Ph |

TABLE A-continued

| No. | R$_1$ | R$_2$ | R$_3$ | R$_9$ | R$_{10}$ |
|---|---|---|---|---|---|
| 090 | C$_3$H$_5$-cycl | H | H | H | 4-Ol-3-F-Ph |
| 091 | H | H | H | H | 4-Cl-3-CH$_3$-Ph |
| 092 | H | H | H | CH$_3$ | 4-Cl-3-CH$_3$-Ph |
| 093 | CH$_3$ | H | H | H | 4-Cl-3-CH$_3$-Ph |
| 094 | CH$_2$CH$_3$ | H | H | H | 4-Cl-3-CH$_3$-Ph |
| 095 | C$_3$H$_7$-i | H | H | H | 4-Cl-3-CH$_3$-Ph |
| 096 | C$_3$H$_5$-cycl | H | H | H | 4-Cl-3-CH$_3$-Ph |
| 097 | H | H | H | H | 4-Cl-3-CF$_3$-Ph |
| 098 | H | H | H | CH$_3$ | 4-Cl-3-CF$_3$-Ph |
| 099 | CH$_3$ | H | H | H | 4-Cl-3-CF$_3$-Ph |
| 100 | CH$_2$CH$_3$ | H | H | H | 4-Cl-3-CF$_3$-Ph |
| 101 | C$_3$H$_7$-i | H | H | H | 4-Cl-3-CF$_3$-Ph |
| 102 | C$_3$H$_5$-cycl | H | H | H | 4-Cl-3-CF$_3$-Ph |
| 103 | H | H | H | H | 4-Br-3-Cl-Ph |
| 104 | H | H | H | CH$_3$ | 4-Br-3-Cl-Ph |
| 105 | CH$_3$ | H | H | H | 4-Br-3-Cl-Ph |
| 106 | CH$_2$CH$_3$ | H | H | H | 4-Br-3-Cl-Ph |
| 107 | C$_3$H$_7$-i | H | H | H | 4-Br-3-Cl-Ph |
| 108 | C$_3$H$_5$-cycl | H | H | H | 4-Br-3-Cl-Ph |
| 109 | H | H | H | H | 3-Br-4-Cl-Ph |
| 110 | H | H | H | CH$_3$ | 3-Br-4-Cl-Ph |
| 111 | CH$_3$ | H | H | H | 3-Br-4-Cl-Ph |
| 112 | CH$_2$CH$_3$ | H | H | H | 3-Br-4-Cl-Ph |
| 113 | C$_3$H$_7$-i | H | H | H | 3-Br-4-Cl-Ph |
| 114 | C$_3$H$_5$-cycl | H | H | H | 3-Br-4-Cl-Ph |
| 115 | H | H | H | H | 4-Br-3-CH$_3$-Ph |
| 116 | H | H | H | CH$_3$ | 4-Br-3-CH$_3$-Ph |
| 117 | CH$_3$ | H | H | H | 4-Br-3-CH$_3$-Ph |
| 118 | CH$_2$CH$_3$ | H | H | H | 4-Br-3-CH$_3$-Ph |
| 119 | C$_3$H$_7$-i | H | H | H | 4-Br-3-CH$_3$-Ph |
| 120 | C$_3$H$_5$-cycl | H | H | H | 4-Br-3-CH$_3$-Ph |
| 121 | H | H | H | H | 4-CF$_3$-Ph |
| 122 | H | H | H | CH$_3$ | 4-CF$_3$-Ph |
| 123 | CH$_3$ | H | H | H | 4-CF$_3$-Ph |
| 124 | CH$_2$CH$_3$ | H | H | H | 4-CF$_3$-Ph |
| 125 | C$_3$H$_7$-i | H | H | H | 4-CF$_3$-Ph |
| 126 | C$_3$H$_5$-cycl | H | H | H | 4-CF$_3$-Ph |
| 127 | H | H | H | H | 4-CF$_3$O-Ph |
| 128 | H | H | H | CH$_3$ | 4-CF$_3$O-Ph |
| 129 | CH$_3$ | H | H | H | 4-CF$_3$O-Ph |
| 130 | CH$_2$CH$_3$ | H | H | H | 4-CF$_3$O-Ph |
| 131 | C$_3$H$_7$-i | H | H | H | 4-CF$_3$O-Ph |
| 132 | C$_3$H$_5$-cycl | H | H | H | 4-CF$_3$O-Ph |
| 133 | H | H | H | H | 4-HC≡CCH$_2$O-Ph |
| 134 | H | H | H | CH$_3$ | 4-HC≡CCH$_2$O-Ph |
| 135 | CH$_3$ | H | H | H | 4-HC≡CCH$_2$O-Ph |
| 136 | CH$_2$CH$_3$ | H | H | H | 4-HC≡CCH$_2$O-Ph |
| 137 | C$_3$H$_7$-i | H | H | H | 4-HC≡CCH$_2$O-Ph |
| 138 | C$_3$H$_5$-cycl | H | H | H | 4-HC≡CCH$_2$O-Ph |
| 139 | H | H | H | H | 4-CH$_3$O-Ph |
| 140 | H | H | H | CH$_3$ | 4-CH$_3$O-Ph |
| 141 | CH$_3$ | H | H | H | 4-CH$_3$O-Ph |
| 142 | CH$_2$CH$_3$ | H | H | H | 4-CH$_3$O-Ph |
| 143 | C$_3$H$_7$-i | H | H | H | 4-CH$_3$O-Ph |
| 144 | C$_3$H$_5$-cycl | H | H | H | 4-CH$_3$O-Ph |
| 145 | H | H | H | H | 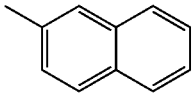 |
| 146 | H | H | H | CH$_3$ | 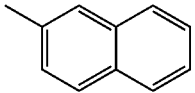 |
| 147 | CH$_3$ | H | H | H | 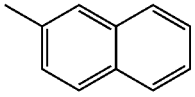 |

TABLE A-continued
| No. | R₁ | R₂ | R₃ | R₉ | R₁₀ |
|---|---|---|---|---|---|
| 148 | CH₂CH₃ | H | H | H | 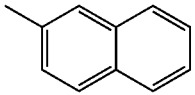 |
| 149 | C₃H₇-i | H | H | H | 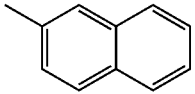 |
| 150 | C₃H₅-cycl | H | H | H | 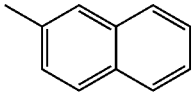 |
| 151 | H | H | H | H | 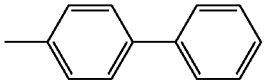 |
| 152 | H | H | H | CH₃ | 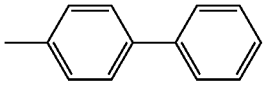 |
| 153 | CH₃ | H | H | H | 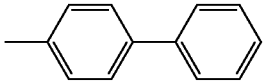 |
| 154 | CH₂CH₃ | H | H | H | 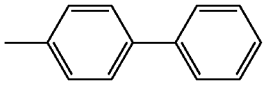 |
| 155 | C₃H₇-i | H | H | H | 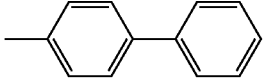 |
| 156 | C₃H₅-cycl | H | H | H | 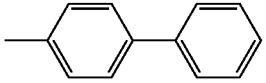 |
| 157 | H | H | H | H | 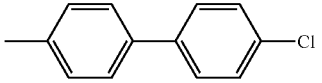 |
| 158 | H | H | H | CH₃ | 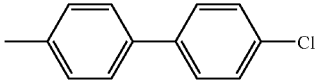 |
| 159 | CH₃ | H | H | H | 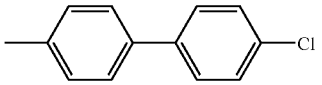 |
| 160 | CH₂CH₃ | H | H | H | 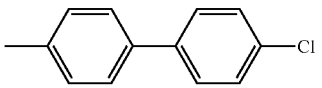 |
| 161 | C₃H₇-i | H | H | H | 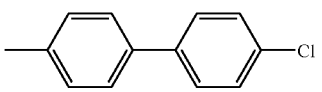 |
| 162 | C₃H₅-cycl | H | H | H | 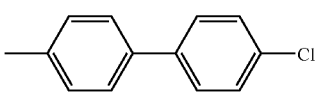 |

TABLE A-continued
| No. | R₁ | R₂ | R₃ | R₉ | R₁₀ |
|---|---|---|---|---|---|
| 163 | H | H | H | H | 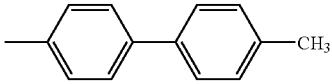—CH₃ |
| 164 | CH₃ | H | H | H | 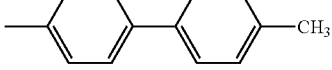—CH₃ |
| 165 | CH₂CH₃ | H | H | H | 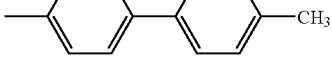—CH₃ |
| 166 | C₃H₇-i | H | H | H | 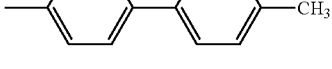—CH₃ |
| 167 | C₃H₅-cycl | H | H | H | —CH₃ |
| 168 | H | H | H | H | 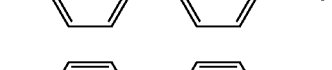—CF₃ |
| 169 | CH₃ | H | H | H | 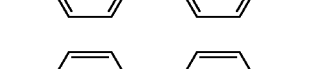—CF₃ |
| 170 | CH₂CH₃ | H | H | H | —CF₃ |
| 171 | C₃H₇-i | H | H | H | —CF₃ |
| 172 | C₃H₅-cycl | H | H | H | 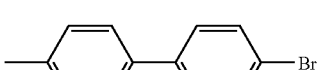—CF₃ |
| 173 | H | H | H | H | 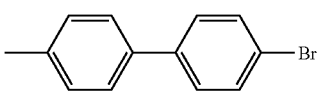—Br |
| 174 | CH₃ | H | H | H | 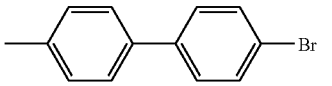—Br |
| 175 | CH₂CH₃ | H | H | H | 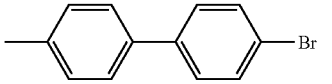—Br |
| 176 | C₃H₇-i | H | H | H | 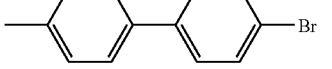—Br |
| 177 | C₃H₅-cycl | H | H | H | —Br |

TABLE A-continued
| No. | R₁ | R₂ | R₃ | R₉ | R₁₀ |
|---|---|---|---|---|---|
| 178 | H | H | H | H | 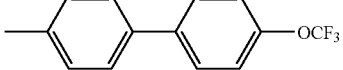 |
| 179 | CH₃ | H | H | H | 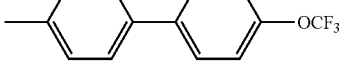 |
| 180 | CH₂CH₃ | H | H | H | 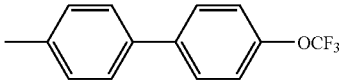 |
| 181 | C₃H₇-i | H | H | H | 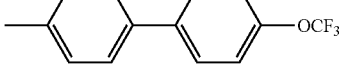 |
| 182 | C₃H₅-cycl | H | H | H | 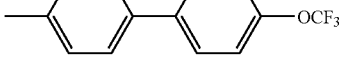 |
| 183 | H | H | H | H | 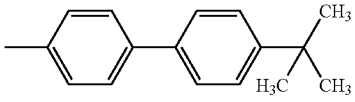 |
| 184 | CH₃ | H | H | H | 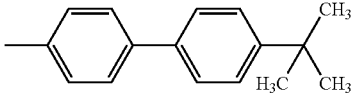 |
| 185 | CH₂CH₃ | H | H | H | 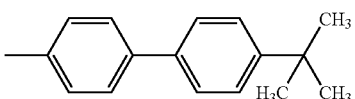 |
| 186 | C₃H₇-i | H | H | H | 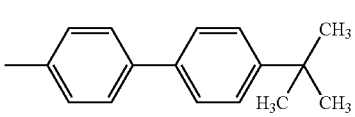 |
| 187 | C₃H₅-cycl | H | H | H | 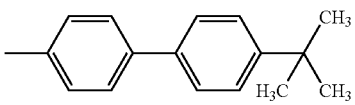 |
| 188 | H | H | H | H | 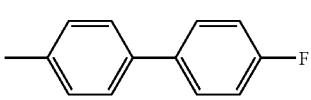 |
| 189 | CH₃ | H | H | H | 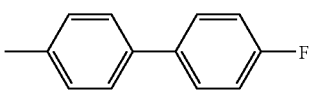 |
| 190 | CH₂CH₃ | H | H | H | 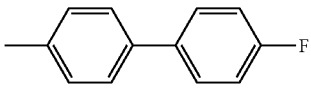 |
| 191 | C₃H₇-i | H | H | H | 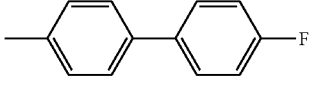 |

TABLE A-continued

| No. | R₁ | R₂ | R₃ | R₉ | R₁₀ |
|---|---|---|---|---|---|
| 192 | C₃H₅-cycl | H | H | H | 4'-fluorobiphenyl |
| 193 | H | H | H | H | 3',4'-dichlorobiphenyl |
| 194 | CH₃ | H | H | H | 3',4'-dichlorobiphenyl |
| 195 | CH₂CH₃ | H | H | H | 3',4'-dichlorobiphenyl |
| 196 | C₃H₇-i | H | H | H | 3',4'-dichlorobiphenyl |
| 197 | C₃H₅-cycl | H | H | H | 3',4'-dichlorobiphenyl |
| 198 | H | H | H | H | 3'-methoxybiphenyl |
| 199 | CH₃ | H | H | H | 3'-methoxybiphenyl |
| 200 | CH₂CH₃ | H | H | H | 3'-methoxybiphenyl |
| 201 | C₃H₇-i | H | H | H | 3'-methoxybiphenyl |
| 202 | C₃H₅-cycl | H | H | H | 3'-methoxybiphenyl |
| 203 | H | H | H | H | 4'-cyanobiphenyl |
| 204 | CH₃ | H | H | H | 4'-cyanobiphenyl |
| 205 | CH₂CH₃ | H | H | H | 4'-cyanobiphenyl |

TABLE A-continued

| No. | $R_1$ | $R_2$ | $R_3$ | $R_9$ | $R_{10}$ |
|---|---|---|---|---|---|
| 206 | $C_3H_7$-i | H | H | H | 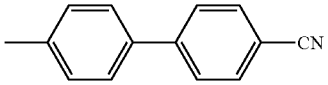 |
| 207 | $C_3H_5$-cycl | H | H | H | 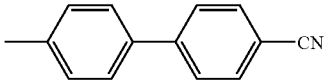 |
| 208 | H | H | H | H | 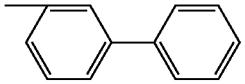 |
| 209 | H | H | H | H | 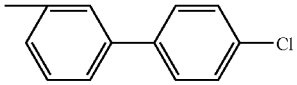 |

Formulations may be prepared analogously to those described in, for example, WO 95/30651.

Bioligical Examples

D-1: Action Against Plasmopara viticola on Vines a) Residual-protective Action

Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and +20° C.

b) Residual-curative Action

Vine seedlings are infected at the 4- to 5-leaf stage with a sporangia suspension of the fungus. After incubation for 24 hours in a humidity chamber at 95–100% relative humidity and +20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 to 41 exhibit a good fungicidal action against *Plasmopara viticola* on vines. Compounds A1.01, A1.02, A1.03, A1.05, A1.07, A2.01 and A2.02 at 200 ppm inhibit fungal infestations in this test by 80% to 100%. At the same time untreated plants showed pathogen attack of 80% to 100%.

D-2: Action Against Phytophthora on Tomato Plants a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and +20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and +20° C.

Compounds of Tables 1 to 41 exhibit a long-lasting effect against fungus infestation. Compounds A1.01, A1.02, A1.03, A1.05, A1.07, A2.01 and A2.02 at 200 ppm inhibit fungal infestations in this test by 80% to 100%. At the same time untreated plants showed pathogen attack of 80% to 100%.

D-3: Action Against Phytophthora on Potato Plants a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and +20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and +20° C.

Compounds of Tables 1 to 41 exhibit a long-lasting effect against fungus infestation.

Compounds A1.01, A1.02, A1.03, A1.04, A1.05, A1.06, A1.07, A2.01 and A2.02 at 200 ppm inhibit fungal infestations in this test by 80% to 100%. At the same time untreated plants showed pathogen attack of 80% to 100%.

What is claimed is:

1. A compound of formula I

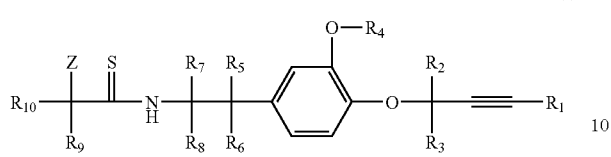

including the optical isomers thereof and mixtures of such isomers, wherein $R_1$ is hydrogen, alkyl, cycloalkyl or optionally substituted aryl, $R_2$ and $R_3$ are each independently hydrogen or alkyl, $R_4$ is alkyl, alkenyl or alkynyl, $R_5$, $R_6$, $R_7$, and $R_8$ are each independently hydrogen or alkyl, $R_9$ is hydrogen, optionally substituted alkyl, optionally substituted alkenyl or optionally substituted alkynyl, $R_{10}$ is optionally substituted aryl or optionally substituted heteroaryl, and Z is hydroxy, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl, optionally substituted alkynylsulfonyl or a group —O—CO—$R_{11}$, —O—CO—O—$R_{11}$ or —O—CO—CO—O—$R_{11}$ wherein $R_{11}$ is hydrogen, optionally substituted alkyl, optionally substituted cycloalkyl, optionally substituted aryl or optionally substituted heteroaryl.

2. A compound according to claim 1 wherein $R_1$ is hydrogen, alkyl, cycloalkyl, phenyl or naphthyl; phenyl and naphthyl being optionally substituted by substituents selected from the group comprising alkyl, alkenyl, alkynyl, cycloalkyl, cycloalkyl-alkyl, phenyl and phenylalkyl, where all these groups may in turn be substituted by one or several halogens; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and $R_2$ and $R_3$ are independently of each other hydrogen or $C_1$–$C_4$alkyl; and $R_4$ is $C_1$–$C_8$alkyl, $C_2$–$C_8$alkenyl, or $C_2$–$C_8$alkynyl; and $R_5$, $R_6$, $R_7$ and $R_8$ are independently of each other hydrogen or $C_1$–$C_4$alkyl; and $R_9$ is hydrogen, $C_1$–$C_4$alkyl, $C_1$–$C_4$haloalkyl, $C_3$–$C_4$alkenyl or $C_3$–$C_4$alkynyl; and $R_{10}$ is aryl or heteroaryl, each optionally substituted with substituents selected from to group comprising alkyl, alkenyl, alkynyl, cycloalkyl, cycloalkyl-alkyl, phenyl and phenylalkyl, where all these groups may be substituted with one or more substituents selected from the group comprising halogen; alkoxy, alkenyloxy, alkynyloxy; alkoxy-alkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl and alkynyloxycarbonyl; and Z is hydroxy, optionally substituted aryloxy or arylthio wherein in each the aryl may be optionally substituted by one or more substituents selected from the group comprising halogen, $C_1$–$C_8$alkoxy, $C_2$–$C_8$alkenyloxy, $C_2$–$C_8$alkynyloxy, $C_1$–$C_8$alkoxy-$C_1$–$C_8$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, di-$C_1$–$C_8$alkylamino, carboxyl and $C_1$–$C_8$alkoxycarbonyl; or is optionally substituted $C_1$–$C_8$alkoxy, optionally substituted $C_2$–$C_8$alkenyloxy, optionally substituted $C_2$–$C_8$alkynyloxy, optionally substituted $C_1$–$C_8$alkylthio, optionally substituted $C_2$–$C_8$alkenylthio, optionally substituted $C_2$–$C_8$alkynylthio, optionally substituted $C_1$–$C_8$alkylsulfinyl, optionally substituted $C_2$–$C_8$alkenylsulfinyl, optionally substituted $C_2$–$C_8$alkynylsulfinyl, optionally substituted $C_1$–$C_8$alkylsulfonyl, optionally substituted $C_2$–$C_8$alkenylsulfonyl; optionally substituted $C_2$–$C_8$alkynylsulfonyl wherein each alkyl, alkenyl or alkynyl group may carry one or more substituents selected from the group comprising halogen, $C_1$–$C_4$alkyl, $C_1$–$C_4$alkoxy, $C_1$–$C_4$alkylthio, $C_3$–$C_6$cycloalkyl, nitro, cyano, hydroxy, phenyl, mercapto, $C_1$–$C_4$alkylcarbonyl and $C_1$–$C_4$alkoxycarbonyl; or is a group —O—CO—$R_{11}$, —O—CO—O—$R_{11}$ or —O—CO—CO—O—$R_{11}$ wherein $R_{11}$ is hydrogen, $C_1$–$C_4$-alkyl or $C_3$–$C_8$-cycloalkyl.

3. A compound according to claim 1 wherein $R_1$ is hydrogen, $C_1$–$C_8$alkyl, $C_3$–$C_8$cycloalkyl, phenyl or naphthyl; phenyl and naphthyl being optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and $R_2$ and $R_3$ are hydrogen; and $R_4$ is $C_1$–$C_6$alkyl; and $R_5$, $R_6$ and $R_7$ are hydrogen and $R_8$ is hydrogen, methyl or ethyl, preferably hydrogen or methyl; and $R_9$ is hydrogen or $C_1$–$C_4$alkyl; and $R_{10}$ is phenyl, naphthyl or biphenyl, each optionally substituted by one to three substituents selected from the group comprising $C_1$–$C_8$alkyl, $C_2$–$C_8$alkenyl, $C_2$–$C_8$alkynyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, $C_1$–$C_8$alkylsulfonyl, halogen, cyano, nitro and $C_1$–$C_8$alkoxycarbonyl; and Z is hydroxy; $C_1$–$C_8$alkoxy, $C_2$–$C_8$alkenyloxy, $C_2$–$C_8$alkynyloxy, $C_1$–$C_8$alkoxy-$C_1$–$C_8$alkoxy, $C_2$–$C_8$alkenyloxy-$C_1$–$C_8$alkoxy, $C_2$–$C_8$alkynyloxy-$C_1$–$C_8$alkoxy, $C_1$–$C_8$haloalkoxy, $C_3$–$C_8$cycloalkyl-$C_1$–$C_8$alkoxy, $C_1$–$C_8$alkylthio, $C_2$–$C_8$alkenylthio, $C_2$–$C_8$alkynylthio, $C_1$–$C_8$haloalkylthio, $C_3$–$C_8$cycloalkyl-$C_1$–$C_8$alkylthio or —O—CO—$C_1$–$C_4$-alkyl.

4. A compound of formula I according to claim 1 wherein $R_1$ is hydrogen, $C_1$–$C_8$alkyl or phenyl optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and $R_2$ and $R_3$ are hydrogen; and $R_4$ is $C_1$–$C_4$alkyl, and $R_5$, $R_6$ and $R_7$ are hydrogen and $R_8$ is hydrogen or methyl; and $R_9$ is hydrogen; and $R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and Z is hydroxy; $C_1$–$C_8$alkoxy, $C_2$–$C_8$alkenyloxy, $C_2$–$C_8$alkynyloxy, $C_1$–$C_4$alkoxy -$C_1$–$C_2$alkoxy, $C_1$–$C_8$alkylthio, $C_2$–$C_8$alkenylthio, $C_2$–$C_8$alkynylthio or —O—CO—$C_1$–$C_4$-alkyl.

5. A compound of formula I according to claim 1 wherein
$R_1$ is hydrogen, $C_1$–$C_8$alkyl or $C_3$–$C_8$cycloalkyl; and
$R_2$, $R_3$, $R_5$, $R_6$, $R_7$, $R_8$ and $R_9$ are hydrogen; and
$R_4$ is methyl or ethyl; and
$R_{10}$ is phenyl, naphthyl, 1,3-biphenyl or 1,4-biphenyl, each optionally substituted by one to three substituents selected from the group comprising $C_1$–$C_8$alkyl, $C_1$–$C_8$haloalkyl, $C_1$–$C_8$alkoxy, $C_1$–$C_8$haloalkoxy, $C_1$–$C_8$alkylthio, $C_1$–$C_8$haloalkylthio, halogen, cyano, nitro and $C_1$–$C_8$alkoxycarbonyl; and
Z is $C_1$–$C_8$alkoxy, $C_2$–$C_6$alkenyloxy, $C_2$–$C_6$alkynyloxy or acetoxy.

6. A compound of formula I according to claim 1 selected from the group comprising
2-(4-bromo-phenyl)-2-hydroxy-N-[2-(3-methoxy-4-prop-2-ynyloxy-phenyl)-ethyl]-thioacetamide,
2-(4-chloro-phenyl)-2-hydroxy-N-[2-(3-methoxy-4-prop-2-ynyloxy-phenyl)-ethyl]-thioacetamide,
2-(3,4-dichloro-phenyl)-2-hydroxy-N-[2-(3-methoxy-4-prop-2-ynyloxy-phenyl)-ethyl]-thioacetamide,
2-hydroxy-2-(4-tolyl)-N-[2-(3-methoxy-4-prop-2-ynyloxy-phenyl)-ethyl]-thioacetamide,
2-(4-ethyl-phenyl)-2-hydroxy-N-[2-(3-methoxy-4-prop-2-ynyloxy-phenyl)-ethyl]-thioacetamide,
2-(4-fluoro-phenyl)-2-hydroxy-N-[2-(3-methoxy-4-prop-2-ynyloxy-phenyl)-ethyl]-thioacetamide,
2-acetoxy-2-(4-bromo-phenyl)-N-[2-(3-methoxy-4-prop-2-ynyloxy-phenyl)-ethyl]-thioacetamide,
2-acetoxy-2-(4-chloro-phenyl)-N-[2-(3-methoxy-4-prop-2-ynyloxy-phenyl)-ethyl]-thioacetamide,
2-acetoxy-2-(3,4-dichloro-phenyl)-N-[2-(3-methoxy-4-prop-2-ynyloxy-phenyl)-ethyl]-thioacetamide,
2-acetoxy-2-(4-tolyl)-N-[2-(3-methoxy-4-prop-2-ynyloxy-phenyl)-ethyl]-thioacetamide,
2-acetoxy-2-(4-ethyl-phenyl)-N-[2-(3-methoxy-4-prop-2-ynyloxy-phenyl)-ethyl]-thioacetamide,
2-acetoxy-2-(4-fluoro-phenyl)-N-[2-(3-methoxy-4-prop-2-ynyloxy-phenyl)-ethyl]-thioacetamide,
2-(4-bromo-phenyl)-2-methoxy-N-[2-(3-methoxy-4-prop-2-ynyloxy-phenyl)-ethyl]-thioacetamide,
2-(4-chloro-phenyl)-2-methoxy-N-[2-(3-methoxy-4-prop-2-ynyloxy-phenyl)-ethyl]-thioacetamide,
2-(3,4-dichloro-phenyl)-2-methoxy-N-[2-(3-methoxy-4-prop-2-ynyloxy-phenyl)-ethyl]-thioacetamide,
2-methoxy-2-(4-tolyl)-N-[2-(3-methoxy-4-prop-2-ynyloxy-phenyl)-ethyl]-thioacetamide,
2-(4-ethyl-phenyl)-2-methoxy-N-[2-(3-methoxy-4-prop-2-ynyloxy-phenyl)-ethyl]-thioacetamide,
2-(4-fluoro-phenyl)-2-methoxy-N-[2-(3-methoxy-4-prop-2-ynyloxy-phenyl)-ethyl]-thioacetamide,
2-(4-bromo-phenyl)-2-ethoxy-N-[2-(3-methoxy-4-prop-2-ynyloxy-phenyl)-ethyl]-thioacetamide,
2-(4-chloro-phenyl)-2-ethoxy-N-[2-(3-methoxy-4-prop-2-ynyloxy-phenyl)-ethyl]-thioacetamide,
2-(3,4-dichloro-phenyl)-2-ethoxy-N-[2-(3-methoxy-4-prop-2-ynyloxy-phenyl)-ethyl]-thioacetamide,
2-ethoxy-2-(4-tolyl)-N-[2-(3-methoxy-4-prop-2-ynyloxy-phenyl)-ethyl]-thioacetamide,
2-(4-ethyl-phenyl)-2-ethoxy-N-[2-(3-methoxy-4-prop-2-ynyloxy-phenyl)-ethyl]-thioacetamide,
2-(4-fluoro-phenyl)-2-ethoxy-N-[2-(3-methoxy-4-prop-2-ynyloxy-phenyl)-ethyl]-thioacetamide,
2-(4-bromo-phenyl)-N-[2-(3-methoxy-4-prop-2-ynyloxy-phenyl)-ethyl]-2-(prop-2-ynyloxy)-thioacetamide,
2-(4-chloro-phenyl)-N-[2-(3-methoxy-4-prop-2-ynyloxy-phenyl)-ethyl]-2-(prop-2-ynyloxy)-thioacetamide,
2-(3,4-dichloro-phenyl)-N-[2-(3-methoxy-4-prop-2-ynyloxy-phenyl)-ethyl]-2-(prop-2-ynyloxy)-thioacetamide,
2-(4-tolyl)-N-[2-(3-methoxy-4-prop-2-ynyloxy-phenyl)-ethyl]-2-(prop-2-ynyloxy) -thioacetamide,
2-(4-ethyl-phenyl)-N-[2-(3-methoxy-4-prop-2-ynyloxy-phenyl)-ethyl]-2-(prop-2-ynyloxy)-thioacetamide,
2-(4-fluoro-phenyl)-N-[2-(3-methoxy-4-prop-2-ynyloxy-phenyl)-ethyl]-2-(prop-2-ynyloxy)-thioacetamide,
2-(4-bromo-phenyl)-N-[2-(3-methoxy-4-pent-2-ynyloxy-phenyl)-ethyl]-2-(prop-2-ynyloxy)-thioacetamide,
2-(4-chloro-phenyl)-N-[2-(3-methoxy-4-pent-2-ynyloxy-phenyl)-ethyl]-2-(prop-2-ynyloxy)-thioacetamide,
2-(3,4-dichloro-phenyl)-N-[2-(3-methoxy-4-pent-2-ynyloxy-phenyl)-ethyl]-2-(prop-2-ynyloxy)-thioacetamide,
2-(4-tolyl)-N-[2-(3-methoxy-4-pent-2-ynyloxy-phenyl)-ethyl]-2-(prop-2-ynyloxy) -thioacetamide,
2-(4-ethyl-phenyl)-N-[2-(3-methoxy-4-pent-2-ynyloxy-phenyl)-ethyl]-2-(prop-2-ynyloxy)-thioacetamide,
2-(4-fluoro-phenyl)-N-[2-(3-methoxy-4-pent-2-ynyloxy-phenyl)-ethyl]-2-(prop-2-ynyloxy)-thioacetamide,
2-(4-bromo-phenyl)-N-[2-(3-methoxy-4-prop-2-ynyloxy-phenyl)-ethyl]-2-(pent-2-ynyloxy)-thioacetamide,
2-(4-chloro-phenyl)-N-[2-(3-methoxy-4-prop-2-ynyloxy-phenyl)-ethyl]-2-(pent-2-ynyloxy)-thioacetamide,
2-(3,4-dichloro-phenyl)-N-[2-(3-methoxy-4-prop-2-ynyloxy-phenyl)-ethyl]-2-(pent-2-ynyloxy)-thioacetamide,
2-(4-tolyl)-N-[2-(3-methoxy-4-prop-2-ynyloxy-phenyl)-ethyl]-2-(pent-2-ynyloxy) -thioacetamide,
2-(4-ethyl-phenyl)-N-[2-(3-methoxy-4-prop-2-ynyloxy-phenyl)-ethyl]-2-(pent-2-ynyloxy)-thioacetamide and
2-(4-fluoro-phenyl)-N-[2-(3-methoxy-4-prop-2-ynyloxy-phenyl)-ethyl]-2-(pent-2-ynyloxy)-thioacetamide.

7. A process for the preparation of a compound of formula I according to claim 1, which comprises sulfurating a compound of formula VI (VI)

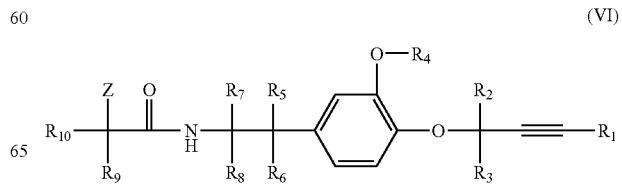

wherein $R_1$, $R_2$, $R_3$, $R_4$, $R_5$, $R_6$, $R_7$, $R_8$, $R_9$, $R_{10}$ and Z are as defined for formula I with a sulfurating agent in an inert diluting agent at temperatures ranging from −80° C. to +200° C.

8. A composition for controlling and protecting against phytopathogenic microorganisms, comprising a compound of formula I according to claim 1 as active ingredient together with a suitable carrier.

9. A method of controlling and preventing an infestation of crop plants by phytopathogenic microorganisms, which comprises the application of a compound of formula I according to claim 1 as active ingredient to the plant, to parts of plants or to the locus thereof.

10. A method according to claim 9, wherein the phytopathogenic microorganisms are fungal organisms.

* * * * *